US009249464B2

(12) United States Patent
Rehli

(10) Patent No.: US 9,249,464 B2
(45) Date of Patent: Feb. 2, 2016

(54) KITS AND METHODS FOR DETECTING METHYLATED DNA

(75) Inventor: Michael Rehli, Regensburg (DE)

(73) Assignee: SEQUENOM, INC., San Diego, CA (US)

( * ) Notice: Subject to any disclaimer, the term of this patent is extended or adjusted under 35 U.S.C. 154(b) by 1582 days.

(21) Appl. No.: 11/720,300

(22) PCT Filed: Nov. 28, 2005

(86) PCT No.: PCT/EP2005/012705
§ 371 (c)(1),
(2), (4) Date: Aug. 16, 2007

(87) PCT Pub. No.: WO2006/056478
PCT Pub. Date: Jun. 1, 2006

(65) Prior Publication Data
US 2009/0130659 A1    May 21, 2009

(30) Foreign Application Priority Data

Nov. 29, 2004  (EP) .................................... 04028268

(51) Int. Cl.
*C12P 19/34* (2006.01)
*C12Q 1/68* (2006.01)
(52) U.S. Cl.
CPC ........ *C12Q 1/6886* (2013.01); *C12Q 2600/154* (2013.01); *C12Q 2600/16* (2013.01)
(58) Field of Classification Search
USPC ............................. 436/501; 435/91.2, 6, 6.12
See application file for complete search history.

(56) References Cited

U.S. PATENT DOCUMENTS

| 4,116,638 | A | 9/1978 | Kenoff et al. |
| 4,608,231 | A | 8/1986 | Witty et al. |
| 5,175,086 | A | 12/1992 | Takekawa et al. |
| 5,399,500 | A | 3/1995 | Oppenheimer et al. |
| 5,441,895 | A | 8/1995 | Jakubowicz et al. |
| 5,639,597 | A | 6/1997 | Lauffer et al. |
| 6,783,759 | B2 | 8/2004 | Rosengard |
| 6,943,240 | B2 | 9/2005 | Bauer et al. |
| 2002/0051974 | A1 | 5/2002 | Dodge et al. |
| 2003/0082600 | A1* | 5/2003 | Olek et al. ........................ 435/6 |
| 2003/0104523 | A1* | 6/2003 | Bauer et al. ................... 435/69.1 |
| 2008/0260743 | A1 | 10/2008 | Rehli |

FOREIGN PATENT DOCUMENTS

| DE | 199 41 756 A1 | 3/2001 |
| EP | 0 322 102 a | 6/1989 |
| EP | 1541668 | 6/2002 |
| JP | 59-147267 A | 8/1984 |
| JP | 61-292556 A | 12/1986 |
| JP | 4-136762 A | 5/1992 |
| JP | 2002-508183 | 3/2002 |
| JP | 2003-125766 | 5/2003 |
| JP | 2004-17 | 1/2004 |
| JP | 2004-532622 | 10/2004 |
| WO | WO99/31241 | 6/1999 |
| WO | WO99/46281 | 9/1999 |
| WO | WO 02/22809 | 3/2002 |
| WO | WO02/068677 | 9/2002 |
| WO | WO 02/101353 A2 | 12/2002 |
| WO | WO03/106612 | 12/2003 |
| WO | WO 2004/058820 A2 | 7/2004 |
| WO | WO 2004/065625 | 8/2004 |
| WO | WO 2006/056478 A1 | 6/2006 |
| WO | WO 2006/056480 A2 | 6/2006 |
| WO | WO 2007/010004 A1 | 1/2007 |
| WO | WO 2007/081791 A2 | 7/2007 |

OTHER PUBLICATIONS

Stratagene catalog, 1988.*
Adler et al., "A real-time immuno-PCR assay for routine ultrasensitive quantification of proteins.", *Biochemical and Biophysical Research Communications*, vol. 308, No. 2, (Aug. 22, 2003), pp. 240-250.
Ballestar et al., "Methyl-CpG-binding proteins. Targeting specific gene repression.", *European Journal of Biochemistry*, vol. 268, No. 1, (Jan. 2001), pp. 1-6.
Ballestar et al., "Methyl-CpG binding proteins identify novel sites of epigenetic inactivation in human cancer.", *The EMBO Journal*, vol. 22, No. 23, (Dec. 1, 2003), pp. 6335-6345.
Brock et al., "A novel technique for the identification of CpG islands exhibiting altered methylation patterns (ICEAMP).", *Nucleic Acids Research*, vol. 29, No. 24, (Dec. 15, 2001), pp. E123.
Catt et al., "Solid-phase radioimmunoassay in antibody-coated tubes.", *Science*, vol. 158, No. 808, (Dec. 22, 1967), pp. 1570-1572.
Cross et al., "Purification of CpG islands using a methylated DNA binding column", *Nature Genetics*, vol. 6, No. 3, (Mar. 1, 1994), pp. 236-244.
Fraga et al., "DNA Methylation: A profile of methods and applications", *Biotechniques*, vol. 33, No. 3, (Sep. 2002), pp. 632, 634, 636-649.
Rauch et al., "Methylated-CpG island recovery assay: a new technique for the rapid detection of methylated-CpG islands in cancer.", *A Journal of Technical Methods and Pathology*, vol. 85, No. 9, (Sep. 2005), pp. 1172-1180.
Sankolli et al., "Improvement in the antibody binding characteristics of microtiter wells by pretreatment with anti-IgG FC immunoglobulin", *Journal of Immunological Methods*, vol. 104, No. 1-2, (1987), pp. 191-194.

(Continued)

*Primary Examiner* — Kenneth R. Horlick
*Assistant Examiner* — Joyce Tung
(74) *Attorney, Agent, or Firm* — Grant IP, Inc.

(57) ABSTRACT

The present invention relates to an in vitro method for detecting methylated DNA comprising (a) coating a container with a polypeptide capable of binding methylated DNA; (b) contacting said polypeptide with a sample comprising methylated and/or unmethylated DNA; and (c) detecting the binding of said polypeptide to methylated DNA. In a preferred embodiment, said method further comprises step (d) analyzing the detected methylated DNA by sequencing. Another aspect of the present invention is a kit for detecting methylated DNA according to the methods of the invention comprising (a) a polypeptide capable of binding methylated DNA; (b) a container which can be coated with said polypeptide; (c) means for coating said container; and (d) means for detecting methylated DNA.

16 Claims, 14 Drawing Sheets

(56) References Cited

OTHER PUBLICATIONS

Figure 1A:
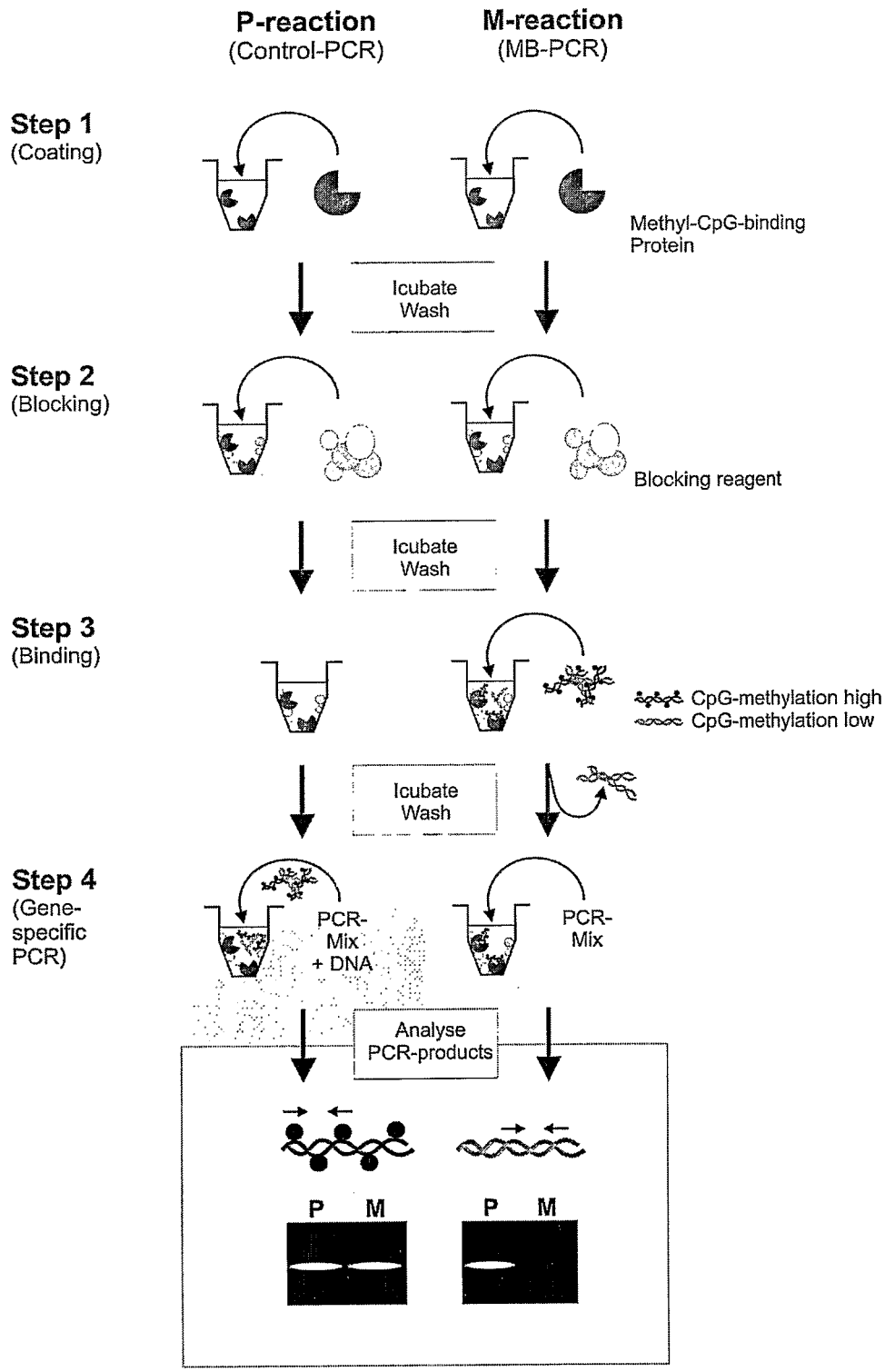

Sano et al., "Detection of heavy methylation in human repetitive DNA subsets by a monoclonal antibody against 5-methylcytosine.", *Biochimica et Biophysica Acta*, vol. 951, No. 1, (Nov. 10, 1988), pp. 157-165.

Shiraishi et al., "Tight interaction between densely methylated DNA fragments and the methyl-CpG binding domain of the rat MeCP2 protein attached to a solid support.", *Biological Chemistry*, vol. 380, No. 9, (Sep. 1999), pp. 1127-1131.

International Search Report for International Application No. PCT/EP2005/012705; mailed May 4, 2006; (4pgs.).

Adorján et al., "Tumour class prediction and discovery by microarray-based DNA methylation analysis," *Nucleic Acids Res.*, 30(5):e21 (2002).

Bestor, "The DNA Methyltransferases of Mammals," *Human Molecular Genetics*, 9(16): 2395-2402 (2000).

Chim et al., "Epigenetic inactivation of INK4/CDK/RB cell cycle pathway in acute leukemias," *Ann. Hematol.*, 82:738-742 (2003).

Claus et al., "Epigenetic targets in hematopoietic malignancies," *Oncogene*, 22:6489-6496 (2003).

Clouaire et al., "Recruitment of MBD1 to target genes requires sequence-specific interaction of the MBD domain with methylated DNA," *Nucleic Acid Research, Advance Access*, 38(4):doi:10.1093/nar/gkq228; published Apr. 8, 2010, © The Author(s) 2010, published by Oxford University Press, 15 pages.

Costello et al., "Aberrant CpG-island methylation has non-random and tumour-type-specific patterns," *Nature Genetics*, 25:132-138 (2000).

Costello et al., "Methylation Matters," *J. Med. Genet.*, 38:285-303 (2001).

Costello et al., "Restriction landmark genome scanning," *Methods*, 27:144-149 (2002).

Dahl et al., "DNA methylation analysis techniques," *Biogerontology*, 4:233-250 (2003).

Detich et al., "Valproate Induces Replication-independent Active DNA Demethylation," *J. Biol. Chem.*, 278(30): 27586-27592 (2003).

Dhasarathy et al., "The MBD protein family-reading an epigenetic mark?," *Mutation Res.*, 647:39-43 (2008).

Dodge et al., "KG-1 and KG-1a model the p15 CpG island methylation observed in acute myeloid leukemia patients," *Leuk. Res.*, 25:917-925 (2001).

Dodge et al., "Selective variegated methylation of the p15 CpG island in acute myeloid leukemia," *Int. J. Cancer*, 78:561-567 (1998).

El-Osta, "DNMT cooperativity—the developing links between methylation, chromatin structure and cancer," *BioEssays*, 25:1071-1084 (2003).

Esteller et al., "A Gene Hypermethylation Profile of Human Cancer," *Cancer Res.*, 61:3225-3229 (2001).

Esteller et al., "Cancer Epigenetics and Methylation," *Science*, 297:1807-1808 (2002).

European Search Report dated May 11, 2005, for European Application No. 04028267.5 (7 pages).

Fahrner et al., "Dependence of Histone Modifications and Gene Expression on DNA Hypermethylation in Cancer," *Cancer Res.*, 62:7213-7218 (2002).

Fatemi et al., "MBD family proteins: reading the epigenetic code," *Journal of Cell Science*, 119(15):3033-3037 (2006).

Frommer et al., "A genomic sequencing protocol that yields a positive display of 5-methylcytosine residues in individual DNA strands," *Proc. Natl. Acad. Sci.*, 89:1827-1831 (1992).

Gagnon et al., "Interaction of 5-aza-2'-deoxycytidine and depsipeptide on antineoplastic activity and activation of 14-3-3sigma, E-cadherin and tissue inhibitor of metalloproteinase 3 expression in human breast carcinoma cells," *Anticancer Drugs*, 14:193-202 (2003).

Ghoshal et al., "Inhibitors of histone deacetylase and DNA methyltransferase synergistically activate the methylated metallothionein I promoter by activating the transcription factor MTF-1 and forming an open chromatin structure," *Mol. Cell. Biol.*, 22(23):8302-8319 (2002).

Gitan et al., "Methylation-specific oligonucleotide microarray: a new potential for high-throughput methylation analysis," *Genome Res.*, 12:158-164 (2001).

Goto et al., "Regulation of X-chromosome inactivation in development in mice and humans," *Microbiol. Mol. Biol. Rev.*, 62(2):362-378 (1998).

Haehnel et al., "Transcriptional regulation of the human *Toll-like receptor 2* gene in monocytes and macrophages," *J. Immunol.*, 168:5629-5637 (2002).

Hendrich et al., "Identification and characterization of a family of mammalian methyl-CpG binding proteins," *Mol. Cell Biol.*, 18(11):6538-6547 (1998).

Hendrich et al, "The methyl-CpG binding domain and the evolving role of DNA methylation in animals," *Trends Genet.*, 19(5):269-277 (2003).

Herman et al., "Gene silencing in cancer in association with promoter hypermethylation," *N. Engl. J. Med.*, 349(21): 2042-2054 (2003).

Hornick et al., "Antibody Affinity-III the Role of Multivalence," *Immunochemistry*, 9:325-330 (1972).

Issa, "Age-related epigenetic changes and the immune system," *Clin. Immunol.*, 109:103-108 (2003).

Issa, "Decitabine," *Curr. Opin. Oncol.*, 15:446-451 (2003).

Issa et al., "The *Estrogen Receptor* CpG Island Is Methylated in Most Hematopoietic Neoplasms," *Cancer Res.*, 56:973-977 (1996).

Jones et al., "Current Trends in Molecular Recognition and Bioseparation, " *J. Chromatography A*, 707:3-22 (1995).

Kalebic, "Epigenetic changes: potential therapeutic targets," *Ann. N.Y Acad. Sci.*, 983:278-285 (2003).

Klose et al., "DNA Binding Selectivity of MeCP2 Due to a Requirement for A/T Sequences Adjacent to Methyl-CpG," *Molecular Cell*, 19:667-678 (2005).

Leone et al., "Inhibitors of DNA methylation in the treatment of hematological malignancies and MDS," *Clin. Immunol.*, 109:89-102 (2003).

Lopez-Serra et al., "Proteins that bind methylated DNA and human cancer: reading the wrong words," *Br. J. Cancer*, 98:1881-1885 (2008).

Lyons et al., "Decitabine: Development of a DNA methyltransferase inhibitor for hematological malignancies," *Curr. Opin. Investig. Drugs*, 4(12):1442-1450 (2003).

Momparler "Cancer epigenetics," *Oncogene*, 22:6479-6483 (2003).

Ng et al., "DNA methylation and chromatin modification," *Curr. Opin. Genet. & Dev.*, 9:158-163 (1999).

Notice of Reasons for Rejection issued in Japanese Patent Application No. 2007-541869, mailed on Jul. 5, 2011, 10 pages (English translation).

Notice of Reasons for Rejection issued in Japanese Patent Application No. 2012-185139, mailed on Feb. 25, 2014, 5 pages.

PCT International Search Report and the Written Opinion of the International Searching Authority for PCT/EP2005/012705, mailed May 4, 2006, 11 pages.

PCT Notification Concerning Transmittal of International Preliminary Report on Patentability with PCT International Preliminary Report on Patentability and Written Opinion issued in International Application No. PCT/EP2005/012707 dated Mar. 6, 2008, 8 pages.

Plass, "Cancer epigenomics," *Hum. Mol. Genet.*, 11(20):2479-2488 (2002).

Razin, "CpG methylation, chromatin structure and gene silencing—a three-way connection," *EMBO J.*, 17(17):4905-4908 (1998).

Robertson et al., "DNA methylation in health and disease" *Nat. Rev. Genet.*, 1:11-19 (2000).

Shaker et al., "Preclinical evaluation of antineoplastic activity of inhibitors of DNA methylation (5-aza-2'-deoxycytidine) and histone deacetylation (trichostatin A, depsipeptide) in combination against myeloid leukemic cells," *Leuk. Res.*, 27:437-444 (2003).

Shi et al., "Oligonucleotide-based microarray for DNA methylation analysis: principles and applications," *J. Cell. Biochem.*, 88:138-143 (2003).

Shiraishi et al., "Isolation of DNA fragments associated with methylated CpG islands in human adenocarcinomas of the lung using a methylated DNA binding column and denaturing gradient gel electrophoresis," *Proc. Natl. Acad. Sci.*, 96:2913-2918 (1999).

(56) References Cited

OTHER PUBLICATIONS

Sims et al., "Histone lysine methylation: a signature for chromatin function," *Trends in Genet.*, 19(11): 629-639 (2003).

Singal et al., "DNA methylation," *Blood*, 93(12):4059-4070 (1999).

Smith et al., "Identification of novel imprinted genes in a genome-wide screen for maternal methylation," *Genome Res.*, 13:558-569 (2003).

Suzuki et al., "A genomic screen for genes upregulated by demethylation and histone deacetylase inhibition in human colorectal cancer," *Nat. Genet.*, 31:141-149 (2002).

Wolffe et al., "DNA demethylation," *Proc. Natl. Acad. Sci.*, 96:5894-5896 (1999).

Yan et al., "Dissecting Complex Epigenetic Alterations in Breast Cancer Using CpG Island Microarrays," *Cancer Res.*, 61:8375-8380 (2001).

Zeschnigk et al., "Imprinted segments in the human genome: different DNA methylation patterns in the Prader-Willi/Angelman syndrome region as determined by the genomic sequencing method," *Hum. Mol. Genet.*, 6(3):387-395 (1997).

Notice of Reasons for Rejection of Japanese Patent Application No. 2007-541868, mailed Nov. 11, 2014, 5 pages.

Sano et al., "Immuno-PCR: very sensitive antigen detection by means of specific antibody-DNA conjugates" Science (1992) 258:120-122.

GenBank Accession No. NM_003927, *Homo sapiens* methyl-CpG binding domain protein 2 (MBD2), transcript variant 1, mRNA, Mar. 15, 2015.

\* cited by examiner

Figure 7 (I)

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccag tgaattttaa cgttgcagga    420
caggatgtgg tgcccgatgt gactagctct ttgctgcagg ccgtcctatc tctggttcc    480
gataagagac ccagaactcc ggccccccac cgcccaccgc cacccccata catatgtggt    540
acgcaagtaa gagtgcctgc gcatgcccca tgtgccccac caagagtttt gcatcccata    600
caagtcccca aagtggagaa ccgaaccaat tcttcgcggg cagaacaaaa gcttctgcac    660
acgtctccac tcgaatttgg agccggccgg cgtgtgcaaa agaggtgaat cgaacgaaag    720
acccgtgtgt aagccgcgt ttccaaaatg tataaaaccg agagcatctg gccaatgtgc     780
atcagttgtg gtcagcagca aaatcaagtg aatcatctca gtgcaactaa agggggggatc    840
cgatctcaat atg aag tta tgc ata tta ctg gcc gtc gtg gcc ttt gtt      889
            Met Lys Leu Cys Ile Leu Leu Ala Val Val Ala Phe Val
              1            5                  10
ggc ctc tcg ctc ggg aga tct cca tgg ccc ggg gta cct act agc acg        937
Gly Leu Ser Leu Gly Arg Ser Pro Trp Pro Gly Val Pro Thr Ser Thr
         15                  20                  25
gag agc ggg aag agg atg gat tgc ccg gcc ctc ccc ccc gga tgg aag        985
Glu Ser Gly Lys Arg Met Asp Cys Pro Ala Leu Pro Pro Gly Trp Lys
 30                  35                  40                  45
aag gag gaa gtg atc cga aaa tct ggg cta agt gct ggc aag agc gat       1033
Lys Glu Glu Val Ile Arg Lys Ser Gly Leu Ser Ala Gly Lys Ser Asp
                 50                  55                  60
gtc tac tac ttc agt cca agt ggt aag aag ttc aga agc aag cct cag       1081
Val Tyr Tyr Phe Ser Pro Ser Gly Lys Lys Phe Arg Ser Lys Pro Gln
             65                  70                  75
ttg gca agg tac ctg gga aat act gtt gat ctc agc agt ttt gac ttc       1129
Leu Ala Arg Tyr Leu Gly Asn Thr Val Asp Leu Ser Ser Phe Asp Phe
         80                  85                  90
aga act gga aag atg atg cct agt aaa tta cag aag aac aaa cag aga       1177
Arg Thr Gly Lys Met Met Pro Ser Lys Leu Gln Lys Asn Lys Gln Arg
 95                  100                 105
ctg cga aac gat cct ctg gcg gcc gcg gat ccc atc gaa ggt cgt ggt       1225
Leu Arg Asn Asp Pro Leu Ala Ala Ala Asp Pro Ile Glu Gly Arg Gly
         110                 115                 120                 125
ggt ggt ggt ggt gat ccc aaa tct tgt gac aaa cct cac aca tgc cca       1273
Gly Gly Gly Gly Asp Pro Lys Ser Cys Asp Lys Pro His Thr Cys Pro
                 130                 135                 140
ctg tgc cca gca cct gaa ctc ctg ggg gga ccg tca gtc ttc ctc ttc       1321
Leu Cys Pro Ala Pro Glu Leu Leu Gly Gly Pro Ser Val Phe Leu Phe
             145                 150                 155
ccc cca aaa ccc aag gac acc ctc atg atc tcc cgg acc cct gag gtc       1369
Pro Pro Lys Pro Lys Asp Thr Leu Met Ile Ser Arg Thr Pro Glu Val
         160                 165                 170
aca tgc gtg gtg gtg gac gtg agc cac gaa gac cct gag gtc aag ttc       1417
Thr Cys Val Val Val Asp Val Ser His Glu Asp Pro Glu Val Lys Phe
 175                 180                 185
aac tgg tac gtg gac ggc gtg gag gtg cat aat gcc aag aca aag ccg       1465
```

Figure 7 (II)

```
                Asn Trp Tyr Val Asp Gly Val Glu Val His Asn Ala Lys Thr Lys Pro
                190             195                 200                 205
cgg gag gag cag tac aac agc acg tac cgt gtg gtc agc gtc ctc acc                1513
Arg Glu Glu Gln Tyr Asn Ser Thr Tyr Arg Val Val Ser Val Leu Thr
                    210                 215                 220
gtc ctg cac cag gac tgg ctg aat ggc aag gag tac aag tgc aag gtc                1561
Val Leu His Gln Asp Trp Leu Asn Gly Lys Glu Tyr Lys Cys Lys Val
                225                 230                 235
tcc aac aaa gcc ctc cca gcc ccc atc gag aaa acc atc tcc aaa gcc                1609
Ser Asn Lys Ala Leu Pro Ala Pro Ile Glu Lys Thr Ile Ser Lys Ala
                    240                 245                 250
aaa ggg cag ccc cga gaa cca cag gtg tac acc ctg ccc cca tcc cgg                1657
Lys Gly Gln Pro Arg Glu Pro Gln Val Tyr Thr Leu Pro Pro Ser Arg
                255                 260                 265
gat gag ctg acc aag aac cag gtc agc ctg acc tgc cta gtc aaa ggc                1705
Asp Glu Leu Thr Lys Asn Gln Val Ser Leu Thr Cys Leu Val Lys Gly
270                 275                 280                 285
ttc tat ccc agc gac atc gcc gtg gag tgg gag agc aat ggg cag ccg                1753
Phe Tyr Pro Ser Asp Ile Ala Val Glu Trp Glu Ser Asn Gly Gln Pro
                    290                 295                 300
gag aac aac tac aag gcc acg cct ccc gtg ctg gac tcc gac ggc tcc                1801
Glu Asn Asn Tyr Lys Ala Thr Pro Pro Val Leu Asp Ser Asp Gly Ser
                305                 310                 315
ttc ttc ctc tac agc aag ctc acc gtg gac aag agc agg tgg cag cag                1849
Phe Phe Leu Tyr Ser Lys Leu Thr Val Asp Lys Ser Arg Trp Gln Gln
                    320                 325                 330
ggg aac gtc ttc tca tgc tcc gtg atg cat gag gct ctg cac aac cac                1897
Gly Asn Val Phe Ser Cys Ser Val Met His Glu Ala Leu His Asn His
                335                 340                 345
tac acg cag aag agc ctc tcc ctg tct ccg ggt aaa tgagctagag                     1943
Tyr Thr Gln Lys Ser Leu Ser Leu Ser Pro Gly Lys
350                 355                 360
ggcccgcggt tcgaaggtaa gcctatccct aaccctctcc tcggtctcga ttctacgcgt             2003
accggtcatc atcaccatca ccattgagtt taaacccgct gatcagcctc gactgtgcct             2063
tctaaggcct gagctcgctg atcagcctcg atcgaggatc cagacatgat aagatacatt             2123
gatgagtttg gacaaaccac aactagaatg cagtgaaaaa aatgctttat ttgtgaaatt             2183
tgtgatgcta ttgctttatt tgtaaccatt ataagctgca ataaacaagt taacaacaac             2243
aattgcattc attttatgtt tcaggttcag ggggaggtgt gggaggtttt ttaaagcaag             2303
taaaacctct acaaatgtgg tatggctgat tatgatcagt cgacctgcag gcatgcaagc             2363
ttggcgtaat catggtcata gctgtttcct gtgtgaaatt gttatccgct cacaattcca             2423
cacaacatac gagccggaag cataaagtgt aaagcctggg gtgcctaatg agtgagctaa             2483
ctcacattaa ttgcgttgcg ctcactgccc gctttccagt cgggaaacct gtcgtgccag             2543
ctgcattaat gaatcggcca acgcgcgggg agaggcggtt tgcgtattgg gcgctcttcc             2603
gcttcctcgc tcactgactc gctgcgctcg tcgttcggc tgcggcgagc ggtatcagct              2663
cactcaaagg cggtaatacg gttatccaca gaatcagggg ataacgcagg aagaacatg              2723
tgagcaaaag gccagcaaaa ggccaggaac cgtaaaaagg ccgcgttgct ggcgtttttc             2783
cataggctcc gcccccctga cgagcatcac aaaaatcgac gctcaagtca gaggtggcga             2843
aacccgacag gactataaag ataccaggcg tttccccctg gaagctccct cgtgcgctct             2903
cctgttccga ccctgccgct taccggatac ctgtccgcct ttctcccttc gggaagcgtg             2963
gcgctttctc atagctcacg ctgtaggtat ctcagttcgg tgtaggtcgt tcgctccaag             3023
ctgggctgtg tgcacgaacc ccccgttcag cccgaccgct gcgccttatc cggtaactat             3083
cgtcttgagt ccaacccggt aagacacgac ttatcgccac tggcagcagc cactggtaac             3143
```

Figure 7 (III)

```
aggattagca gagcgaggta tgtaggcggt gctacagagt tcttgaagtg gtggcctaac   3203
tacggctaca ctagaaggac agtatttggt atctgcgctc tgctgaagcc agttaccttc   3263
ggaaaaagag ttggtagctc ttgatccggc aaacaaacca ccgctggtag cggtggtttt   3323
tttgtttgca agcagcagat tacgcgcaga aaaaaaggat ctcaagaaga tcctttgatc   3383
ttttctacgg ggtctgacgc tcagtggaac gaaaactcac gttaagggat tttggtcatg   3443
agattatcaa aaaggatctt cacctagatc cttttaaatt aaaaatgaag ttttaaatca   3503
atctaaagta tatatgagta aacttggtct gacagttacc aatgcttaat cagtgaggca   3563
cctatctcag cgatctgtct atttcgttca tccatagttg cctgactccc cgtcgtgtag   3623
ataactacga tacgggaggg cttaccatct ggccccagtg ctgcaatgat accgcgagac   3683
ccacgctcac cggctccaga tttatcagca ataaaccagc cagccggaag ggccgagcgc   3743
agaagtggtc ctgcaacttt atccgcctcc atccagtcta ttaattgttg ccgggaagct   3803
agagtaagta gttcgccagt taatagtttg cgcaacgttg ttgccattgc tacaggcatc   3863
gtggtgtcac gctcgtcgtt tggtatggct tcattcagct ccggttccca acgatcaagg   3923
cgagttacat gatcccccat gttgtgcaaa aaagcggtta gctccttcgg tcctccgatc   3983
gttgtcagaa gtaagttggc cgcagtgtta tcactcatgg ttatggcagc actgcataat   4043
tctcttactg tcatgccatc cgtaagatgc ttttctgtga ctggtgagta ctcaaccaag   4103
tcattctgag aatagtgtat gcggcgaccg agttgctctt gcccggcgtc aatacgggat   4163
aataccgcgc cacatagcag aactttaaaa gtgctcatca ttggaaaacg ttcttcgggg   4223
cgaaaactct caaggatctt accgctgttg agatccagtt cgatgtaacc cactcgtgca   4283
cccaactgat cttcagcatc ttttactttc accagcgttt ctgggtgagc aaaaacagga   4343
aggcaaaatg ccgcaaaaaa gggaataagg gcgacacgga aatgttgaat actcatactc   4403
ttcctttttc aatattattg aagcatttat cagggttatt gtctcatgag cggatacata   4463
tttgaatgta tttagaaaaa taaacaaata ggggttccgc gcacatttcc ccgaaaagtg   4523
ccacctgacg tctaagaaac cattattatc atgacattaa cctataaaaa taggcgtatc   4583
acgaggccct ttcgt                                                    4598
```

Figure 8
A
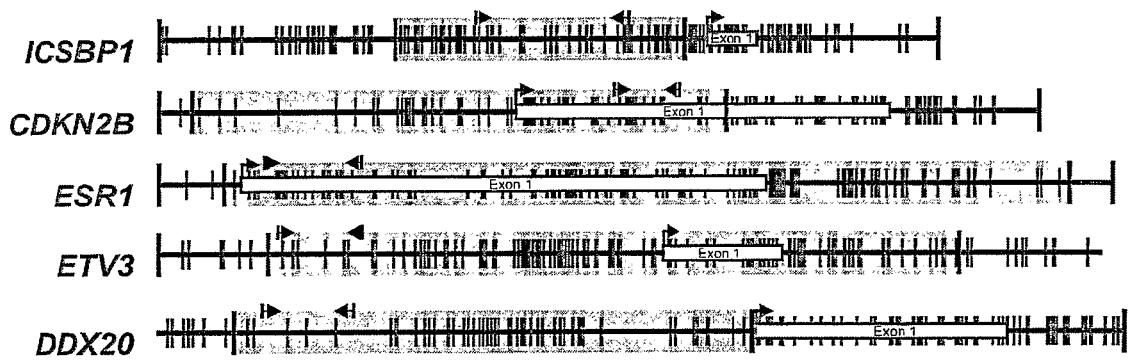
B
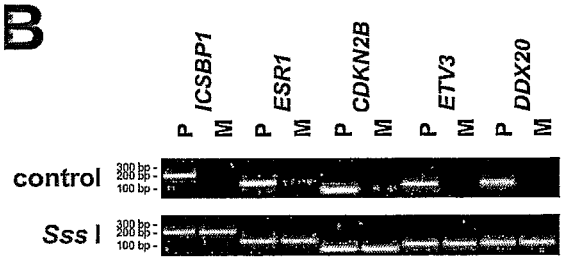

KITS AND METHODS FOR DETECTING METHYLATED DNA

The present invention relates to an in vitro method for detecting methylated DNA comprising (a) coating a container with a polypeptide capable of binding methylated DNA; (b) contacting said polypeptide with a sample comprising methylated and/or unmethylated DNA; and (c) detecting the binding of said polypeptide to methylated DNA. In a preferred embodiment, said method further comprises step (d) analyzing the detected methylated DNA by sequencing. Another aspect of the present invention is a kit for detecting methylated DNA according to the methods of the invention comprising (a) a polypeptide capable of binding methylated DNA; (b) a container which can be coated with said polypeptide; (c) means for coating said container; and (d) means for detecting methylated DNA.

The information to make the cells of all living organisms is contained in their DNA. DNA is made from 4 bases abbreviated as G, A, T, and C, and is built like a very long ladder with pairs of these letter making up each of the "rungs" of the ladder. The letter G pairs with C and A with T. Strings of these pairs store information like a coded message, with the information to make specific molecules grouped into regions called genes. Every cell of diploid animals contains two copies of every gene, with one copy of each gene coming from the mother and one copy from the father. (The only exceptions to this rule are genes on chromosomes that determine whether organisms develop as a "male" or a "female".)

DNA Methylation and Gene Regulation

Apart from the four bases—adenine, guanine, cytosine and thymine—that "spell" our genome, there also is a fifth base which is produced by the modification of the post-replicative DNA. DNA methyl transferases (DNMTs) can catalyse the transfer of a methyl group from the methyl donor S-adenosylmethionine to the cytosine ring, and thereby produce the base 5-methylcytosine. Specific cytosine residues are modified in mammals, which precede a guanosine residue in the DNA sequence (CpG dinucleotide) (Singal, Blood 93 (1999), 4059-4070); Robertson, Nat. Rev. Genet. 1 (2000), 11-19; Ng, Curr. Opin. Genet. Dev. (2000), 158-163; Razin, EMBO J. 17 (1998), 4905-4908). The methylation of CpG dinucleotides generally correlates with stable transcriptional repression and presumably leads to the fact that large parts of the non-coding genome and potentially harmful sequences such as transposons, repeats or viral inserts are not transcribed. It is interesting that CpG dinucleotides are very unevenly distributed in the genome (Singal (1999), loc. cit., Robertson (2000), loc. cit., Ng (2000), loc. cit., Razin (1998), loc. cit.). A large part of the genome contains much fewer CpGs than is statistically expected. This is presumably due to the fact that 5-methylcytosine deaminates comparatively easily to thymidine, which, in the course of evolution, leads to a relative decrease in the number of CpG dinucleotides. There are, however, again and again, larger numbers of CpGs distributed within the genome, so-called CpG islands. These regions often contain transcription initiation points and gene promoters and are generally not methylated in contrast to the CpGs which are not associated with CpG islands. In normal cells, the methylation of CpG islands has been observed only in exceptional cases such as the inactivation of the second copy of the x-chromosome in female cells and the parental imprinting genome (Singal (1999), loc. cit., Robertson (2000), loc. cit., Ng (2000), loc. cit., Razin (1998), loc. cit.).

Regulation of DNA Methylation

It is only partly understood how DNA methylation patterns are established in the course of the embryogenesis and how the CpG methylation is maintained and regulated in the genome (Singal (1999), loc. cit., Ng (2000), loc. cit., Razin (1998), loc. cit.). In mammal species, there are three DNA methyl transferases known (DNMT1, 3a and 3b) which catalyse the DNA methylation process. The corresponding share that each DNMT contributes to the maintenance and regulation of the CpG methylation must, however, still be clarified. Yet, all three enzymes are obviously essential to embryogenesis, the corresponding knockout mice die in utero or shortly after birth (Bestor, Hum. Mol. Genet. 9 (2000), 2395-2402; El Osta, Bioessays 25 (2003), 1071-1084). In the meantime, the connection between DNA methylation, modifications of the chromatin structure and certain histone modifications has been shown several times. The methylation of DNA mostly correlates with histone deacetylation and methylation of the lysine 9 residue at histone H3 (Sims, Trends Genet. 19 (2003), 629-639, Fahrner, Cancer Res. 62 (2002), 7213-7218). Accordingly, DNMTs are associated with histone acetylases (HDACs) or co-repressor complexes. It is also hardly known how methyl groups are removed from CpG residues. In proliferating cells, the DNA methylation can probably also take place passively during replication. There are, however, also examples of DNA demethylation in post-mitotic cells which can be explained by the existence of an active, yet unknown demethylase (Wolffe, Proc. Natl. Acad. Sci. 96 (1999), 5894-5896).

CpG Methylation and Gene Silencing

Methylation of promoters (but not of non-regulating sequences) correlates with stable, transcriptional repression (Singal (1999), loc. cit., Ng (2000), loc. cit., Razin (1998), loc. cit.). The repressive properties of 5-methylcytosine can be mediated by two mechanisms. Firstly, the DNA methylation can directly impair the binding of transcription factors. The second possibility, which is likely to be responsible for the largest part of repression, is the recruitment of methyl-CpG-binding proteins (MBPs) (Ballestar, Eur. J. Biochem. 268 (2001), 1-6). MBPs such as MECP2 or MBD2 (a component of the MeCP1 complex) are accompanied by co-repressor complexes and HDACs which have a repressive effect and are responsible for the formation of dense chromatin structures inaccessible to transcription factors (heterochromatin) (Ballestar (2001), loc. cit.).

Epigenetic Changes in Tumorigenesis

It keeps becoming clearer that the formation of tumours is supported not only by genetic lesions (e.g. mutations or translocations) but also by epigenetic changes. An abnormal chromatin structure or DNA methylation can influence the transcriptional status of oncogenes or tumour suppressor genes and can promote tumour growth. Changes in the DNA methylation include either the loss of methylation in normally methylated sequences (hypomethylation) or the methylation of normally unmethylated sequences (hypermethylation) (Roberston (2000), loc. cit., Herman, N. Engl. J. Med. 349 (2003), 2042-2054; Momparler, Oncogene 22 (2003), 6479-6483; Esteller, Science 297 (2002), 1807-1808; Plass, Hum. Mol. Genet. 11 (2002), 2479-2488).

Hypomethylation

A global DNA hypomethylation has been described for almost all kinds of tumours. In tumour tissue, the content in 5-methylcytosine is reduced compared to normal tissue with the major share of demethylation events being found in repetitive satellite sequences or in centromer regions of the chromosomes. However, in single cases, the demethylation and activation of proto-oncogenes such as, e.g., bcl-2 or c-myc have also been described (Costello, J. Med. Genet. 38 (2001), 285-303).

Hypermethylation of CpG Islands

CpG islands in general exert gene regulatory functions. This is why a change in the status of methylation correlates mostly directly with a change in the transcriptional activity of the locus concerned (Robertson (1999); Herman (2003); Esteller (2002); Momparler (2003); Plass (2002), all loc. cit.). Most CpG islands are present in unmethylated form in normal cells. In certain situations, CpG islands can, however, also be methylated in gene regulatory events. The majority of CpG islands of the inactivated X-chromosome of a female cell are, for example, methylated (Goto, Microbiol. Mol. Biol. Rev. 62 (1998), 362-378). CpG islands can be methylated also in the course of normal aging processes (Issa, Clin. Immunol. 109 (2003), 103-108).

It is in particular in tumours that CpG islands which are normally not methylated can be present in a hypermethylated form. In many cases, genes affected by the hypermethylation encode proteins which counteract the growth of a tumour such as, e.g., tumour suppressor genes. The following Table lists examples of genes for which it could be shown that they can be inactivated in tumours through the epigenetic mechanism of hypermethylation.

TABLE

Hypermethylated genes in tumours (examples)

| | gene | chromo-some | function |
| --- | --- | --- | --- |
| cell cycle control | p16 | 9p21 | cycline-dependent kinase inhibitor |
| | p15 | 9p21 | cycline-dependent kinase inhibitor |
| | Rb | 13q14 | cell cycle inhibition |
| | p73 | 1p36 | p53-like protein |
| DNA repair | MLH1 | 3p21 | DNA mismatch repair protein |
| | GSTPI | 11q13 | inhibitor of oxidative DNA damage |
| | O6-MGMT | 10q26 | DNA methyltransferase |
| | BRCA1 | 17q21 | DNA repair protein |
| apoptosis | TMS-1/ASC | 16p12-p11 | adaptor for caspase 1 |
| | caspase 8 | 2q33-q34 | PCD initiator (Fas, Trail, TNF, . . .) |
| | DAPK1 | 9q34 | PCD by IFNγ |
| invasion/architec-ture | E-cadherin | 16q22 | adhesion molecule |
| | VHL | 3p26-p25 | angiogenesis-promoting protein |
| | TIMP-3 | 22q12-q13 | metalloproteinase inhibitor |
| | THBS1 | 15q15 | angiogenesis inhibitor |
| growth factor response | ER-α | 6q25 | estrogen receptor |
| | RAR-β | 3p24 | retinoic acid receptor |
| | SOCS-1 | 16p13 | neg. regulator in the JAK/STAT signal path |

Reasons for the tumour-specific hypermethylation are almost unknown. Interestingly, certain kinds of tumours seem to have their own hypermethylation profiles. It could be shown in larger comparative studies that hypermethylation is not evenly distributed but that it occurs depending on the tumour. In cases of leukaemia, mostly other genes are hypermethylated compared to, for instance, colon carcinomas or gliomas. Thus, hypermethylation could be useful for classifying tumours (Esteller, Cancer Res. 61 (2001), 3225-3229; Costello, Nat. Genet. 24 (2000), 132-138).

In many cases, hypermethylation is also combined with an increased activity of HDACs. After treatment with demethylating substances (e.g. 5-azacytidine), many methylated genes could only be reactivated after also using HDAC inhibitors (such as, e.g., trichostatin A (TSA)) (Suzuki, Nat. Genet. 31 (2002), 141-149; Ghoshal, Mol. Cell. Biol. 22 (2002), 8302-8319; Kalebic, Ann. N.Y. Acad. Sci. 983 (2003), 278-285).

Most analyzes suggest that the DNA methylation is dominantly repressed and that it cannot be reversed by a treatment with HDAC inhibitors such as TSA (Suzuki (2002); Ghoshal (2002), loc. cit.). There are, however, also more recent indications that valproate, a HDAC inhibitor which is already used in clinics, can lead to the demethylation of DNA (Detich, J. Biol. Chem. 278 (2003), 27586-27592). However, no systematic analyzes have so far been carried out in this respect.

Clinical Approaches for Reversing Epigenetic Changes

While genetic causes of cancer (such as, e.g., mutations) are irreversible, epigenetic changes contributing their share to the tumorigenesis might possibly be reversible. Thus, the possible treatment of epitgenetic changes offers new possibilities of therapy for the treatment of neoplasias (Herman (2003); Momparler (2003); Plass (2002), all loc. cit.; Leone, Clin. Immunol. 109 (2003), 89-102; Claus, Oncogene 22 (2003), 6489-6496).

More than 20 years ago, 5-azacytidine has already been developed as an anti-neoplastic medicament and used without the molecular effect of the substance being known. Nowadays, it is already used successfully in a further developed form (Deoxy-5-azacytidine, Decitabine) for the treatment of myelodysplastic syndromes and secondary leukaemia (Leone (2003), loc. cit.; Lyons, Curr. Opin. Investig. Drugs 4 (2003), 1442-1450; Issa, Curr. Opin. Oncol. 15 (2003), 446-451). Due to the in vitro observation that HDAC inhibitors can support the reactivation of methylated promoters and can act synergistically with demethylated substances, at present pilot studies are carried out throughout the world, combining the use of both classes of substances (Kalebic (2003); Claus (2003), loc. cit.; Gagnon, Anticancer Drugs 14 (2003), 193-202; Shaker, Leuk. Res. 27 (2003), 437-444).

Detection Methods for the Analyzis of CpG Methylation

The development of detection methods for the analyzis of genomic CpG methylation has mainly gained importance due to the fact that it has been found that changes in the CpG methylation pattern can be associated with diseases such as cancer. At present, there are mainly techniques known which are used for the detection of the CpG methylation of known gene loci (Dahl, Biogerontology 4 (2003), 233-250). Methods allowing an analyzis of the CpG methylation throughout the genome are less established. In the following, the most common methods for analyzis of CpG methylation together with their main fields of application are summarised.

Use of Methylation-sensitive Restriction Enzymes for the Detection of CpG Methylation The methylation status of specific CpG dinucleotides can be determined using isoschizomers of bacterial restriction endonucleases which are characterised by different sensitivities vis-à-vis 5-methylcytosine. Examples thereof are the enzymes HpaII and MspI—both cut CCGG sequences, HpaII however only if the internal cytosine is not methylated. Some assays are based on the use of methylation-sensitive restriction enzymes, said assays being used for both the analyzis of individual genes and analyzis of the CpG methylation throughout the genome. The fragments of a methylation-sensitive restriction digestion are mostly detected by means of Southern blot or a genomic PCR of the region flanking the restriction site (Dahl (2003), loc. cit.). All analyzes of the CpG methylation throughout the genome, which have been published up to today, use methylation-sensitive restriction enzymes as a component of the method. Restriction Landmark Genomic Scanning (RLGS) (Costello, Methods 27 (2002), 144-149), for instance, uses a kind of two-dimensional agarose gel electrophorese in which every dimension is digested with a different methylation-sensitive restriction enzyme to identify differences in the CpG methylation of two DNA populations. Methylated CpG Island Amplification (MCA) enriches fragments with methylated SmaI restriction sites and uses LM-PCR for enriching the fragments. Such amplification products have already been successfully analyzed by means of Representational Difference Analyzis (RDA) (Smith, Genome Res. 13 (2003), 558-569) or CpG island microarrays (Yan, Cancer Res. 6 (2001), 8375-8380).

With regard to the analyzis of the CpG methylation throughout the genome, all assays that are based on methylation-sensitive restriction enzymes have disadvantages. In order to carry out the assays in an optimal way, it has, amongst others, to be guaranteed that all restriction digestions are completed. The greatest disadvantage is that the analyzes merely inform on the methylation status of the cytosine residues which have been recognised by the methylation-sensitive restriction enzymes used. The selection of the restriction enzymes automatically limits the number of detectable sequences—a neutral analyzis of the CpG methylation is therefore not possible.

Bisulfate Treatment for the Analyzis of the CpG Methylation

The treatment of double-stranded genomic DNA with sodium bisulfate leads to the deamination of unmethylated cytosine residues into uracil residues and to the formation of two single strands that are no longer complementary. During this treatment, 5-methyl cytosine is maintained. The differences in sequence produced in this way form the basis of the differentiation between methylated and unmethylated DNA (Frommer, Proc. Natl. Acad. Sci. 889 (1992), 1827-1831). DNA treated with bisulfite can be used directly in PCR in which uracil residues (previously unmethylated cytosine) and thymidine residues are amplified as thymidine and only 5-methylcytosine residues are amplified as cytosine residues. Depending on the application, the primers used for the PCR differentiate between methylated and unmethylated sequences or amplify fragments independently of the methylation status. PCR fragments which have been amplified using non-discriminating primers can, for instance, be sequenced directly to determine the share in methylated and unmethylated CpGs. Further methods make use of the physical differences of such PCR fragments (melting behaviour, single-strand conformation, restriction sites for restriction enzymes, etc.) for determining the degree of methylation (Dahl (2003), loc. cit.). Other methodical approaches that allow high throughput methylation analyzes utilise the differences in sequence for the specific amplification of methylated and unmethylated sequences by discriminating primers or probes (methylation-specific PCR, methylight PCR) (Dahl (2003), loc. cit.). Bisulfite-induced differences in the sequence of PCR products can also be found by means of methylation-specific oligonucleotide (MSO) microarrays (Shi, J. Cell. Biochem. 88 (2003), 138-143; Adorjan, Nucleic Acid Res. 30 (2002), e21; Gitan, Genome Res. 12 (2002), 158-164).

In contrast to the methylation-sensitive restriction enzymes, the DNA treated with bisulfite can provide information on the methylation status of several CpG residues in an amplified genomic fragment. The detection of CpG methylation by using discriminating primers or probes, however, is limited to the methylation status of single (or few) cytosine residues. Hence, the information provided by all presently known assays of the prior art that are suitable for high throughput methylation analyzis of single gene loci is limited to one or only a few CpG residues within the gene of interest.

Further Methods for the Detection of CpG Methylation

Antibodies against 5-methyl cytosine recognise CpG methylation in denatured, single-stranded DNA are used mainly for the immunohistochemical staining of the CpG methylation on the chromosomes of individual, fixed cells.

Already in 1994, the laboratory of A. Bird developed a method for enriching methylated DNA fragments by means of affinity chromatography (Gross, Nat. Genet. 6 (1994), 236-244). A recombinant MECP2 bound to a matrix was used for binding the methylated DNA. Since then this technique has been used, improved and combined with further techniques by other working groups (Shiraishi, Proc. Natl. Acad. Sci. 96 (1999), 2913-2918; Brock, Nucleic Acid. Res. 29 (2001), E123). The binding of strongly or less strongly methylated genomic sequences to an affinity matrix depends on the salt concentration which makes it possible to separate the CpG islands with dense methylation from other sequences with a lower methylation density. The disadvantage of this affinity chromatography is the large amount of genomic DNA required (50-100 μg) and the relatively time-consuming procedure.

In view of the foregoing, it is evident that methylation of CpG dinucleotides is an important epigenetic mechanism for controlling transcriptional activity of a cell. Generally, methylation of CpG dinucleotides correlates with transcriptional inactivity. Yet, during normal or degenerated differentiation processes the methylation pattern of genloci may change. Accordingly, the reversal of normal methylation patterns during tumorigenesis can lead to an abnormal repression (or activation) of genes, for instance, tumor suppressor genes or oncogenes, respectively, and, thus, leading to tumorigenesis. Hence, the detection of CpG methylated DNA und thus the identification of misregulated tumor-suppressor genes and/or oncogenes is of outmost clinical interest. As mentioned above, the prior art describes different approaches for the detection of methylated DNA which, however, suffer from certain shortcomings. For example, the methods of the prior art may not be suitable for high-through put applications or may not reliable detect CpG methylated DNA, particularly if only low amounts of DNA can be made subject of an analyzis. Thus, there is still a need for further means and methods for detecting methylated DNA which may overcome the shortcomings and drawbacks of the prior art. Accordingly, the technical problem underlying the present invention is to comply with the needs described above.

The solution to this technical problem is achieved by providing the embodiments characterized in the claims.

Accordingly, in a first aspect the present invention relates to an in vitro method for detecting methylated DNA comprising (a) coating a container with a polypeptide capable of binding methylated DNA;

(b) contacting said polypeptide with a sample comprising methylated and/or unmethylated DNA; and (c) detecting the binding of said polypeptide to methylated DNA.

As documented in the appended Examples, it was surprisingly found that a single-tube assay/in vitro method can be safely and reliable employed in the detection of methylated nucleic acid molecules, in particular CpG-methylated DNA molecules/DNA fragments. The advantages of said method are its fast, sensitive, and reliable detection of preferably methylated DNA and its ability to analyze target DNA fragments according to their methylation degree. In contrast to the prior art, the method provided herein does not require bisulfite treatment or methylation-sensitive restriction and is not limited to detecting single/few CpG residues. The information provided may actually be more relevant than that of other methods of the prior art, since, methylation density of a proximal promoter can correlate better with the transcriptional status of a gene than the methylation status of a-single CpG residue within the region. Accordingly, a "single-tube"

assay is provided herein, wherein the degree of methylation may be estimated relative to a PCR reaction of the (genomic) input DNA.

A preferably homogeneously coated container in accordance with this invention, preferably, facilitates that a polypeptide which is capable of binding methylated DNA and which is employed in accordance with the method described herein has a maximum binding capacity for methylated DNA. A homogenous coating of the container can be achieved by methods known in the art and preferably by the method of the present invention described herein and/or in the appended Examples. Further, homogeneous coating can be controlled by methods known in the art, such as Coomassie-Blue staining. The term "container" encompasses any container which is commonly used and/or suitable for scientific and/or diagnostic purposes. Preferably, said container is composed of the following materials: polystyrene, polyvinyl chloride or polypropylene or the like, more preferably it is composed of polycarbonate. It is also preferred that polystyrene, polyvinyl chloride, polypropylene or polycarbonate is thermocycler-compatible, i.e. it is preferably heat-stable and/or durable at different temperatures for different time intervals. It is moreover preferred that polystyrene, polyvinyl chloride, polypropylene or polycarbonate are inert to chemical and/or biological agents used in connection with the method of the present invention.

So far, coatable PCR-tubes have only been used for immuno-polymerase chain reaction (immuno-PCR) (Sano, Science 258 (1992); Adler, Biochem Biophys Res Commun. 308 (2003), 240-250). Immuno-PCR is an antigen detection system, in which a specific DNA molecule is used as the marker. A streptavidin-protein A chimera that possesses tight and specific binding affinity both for biotin and immunoglobulin G is used to attach a biotinylated DNA specifically to antigen-monoclonal antibody complexes that are immobilized on microtiter plate wells. Then, a segment of the attached DNA is then amplified by PCR. Immuno-PCR is comparable to traditional ELISA techniques and uses the sandwich-approach with a more sensitive detection system (PCR detection of the marker DNA). Thus, in contrast to the present invention, where DNA is the direct subject of detection, Immuno-PCR uses DNA as a means (marker) to detect an antigen.

The term "coating" means that the surface of the container is preferably entirely coated with a polypeptide which is capable of binding methylated DNA, whereby essentially identical amounts of said polypeptide are present in each and every area of the surface of said container. Examples of such binding polypeptides are given herein below and comprise, inter alia and preferably, a polypeptide belonging to the Methyl-DNA binding protein (MBD) family, and most preferably a bifunctional polypeptide comprising the DNA-binding domain of a protein belonging to the family of Methyl-CpG binding proteins (MBDs) and an Fc portion of an antibody. Said DNA-binding domain is described herein below. Optionally, said bifunctional polypeptide comprises a polypeptide linker which is described herein below. Accordingly, said bifunctional polypeptide is preferably characterized by the amino acid sequence shown in SEQ ID NO: 2 (FIG. 7) which is encoded by the nucleotide sequence shown in SEQ ID NO: 1 (FIG. 7)

The term "polypeptide capable of binding methylated DNA" encompasses any polypeptide which can bind methylated DNA as described herein. The capability of binding methylated DNA can be tested by methods known in the art. The term "polypeptide" when used herein means a peptide, a protein, or a polypeptide which are used interchangeable and which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. As mentioned the terms polypeptide and protein are often used interchangeably herein. The term polypeptide also refers to, and does not exclude, modifications of the polypeptide. Modifications include glycosylation, acetylation, acylation, phosphorylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York (1983), pgs. 1-12; Seifter, Meth. Enzymol. 182 (1990); 626-646, Rattan, Ann. NY Acad. Sci. 663 (1992); 48-62. Preferably, the term "polypeptide" encompasses a polypeptide capable of binding methylated DNA. Said term also encompasses a bifunctional polypeptide which is capable of binding methylated DNA and it encompasses an anti-methylated DNA antibody. Such polypeptides are described herein and are employed in the method of the present invention for detecting methylated DNA.

A "bifunctional polypeptide" means that a polypeptide has, in addition to binding to methylated DNA, preferably to CpG methylated DNA, due to an Fc portion of an antibody which is part of the said bifunctional polypeptide, further capabilities. For example, said Fc portion preferably offers the possibility to conjugate, link or covalently couple (a) compound(s) or moieties to said Fc portion. As used herein, the term "covalently coupled" means that the specified compounds or moieties are either directly covalently bonded to one another, or else are indirectly covalently joined to one another through an intervening moiety or moieties, such as a bridge, spacer, or linkage moiety or moieties. Furthermore, said Fc portion may be used to couple said bifunctional polypeptide to a container as is described herein. A preferred bifunctional polypeptide is characterized by the amino acid sequence shown in SEQ ID NO: 2 (FIG. 7). Further preferred bifunctional polypeptides are described herein below.

Without being bound by theory, it is believed that the nascent bifunctional polypeptide comprising an methyl-DNA-binding domain and an Fc portion of an antibody is folded within a host cell such that preferably two polypeptides are joined at their Fc portion in a manner similar or, preferably, identical to the constant region of an antibody, resulting in a bifunctional polypeptide as described herein.

It was surprisingly found that said bifunctional polypeptide, preferably behaving as an antibody-like protein can preferably bind CpG methylated DNA in an antibody-like manner. That means, the bifunctional polypeptide has a high affinity and high avidity to its "antigen" which is preferably methylated DNA that is preferably methylated at CpG dinucleotides. Again, without being bound by theory, the high affinity and avidity of the bifunctional polypeptide employed in the method of the present invention for detecting methylated DNA for its "antigen" is caused by the unique structure of said bifunctional polypeptide. This is because, it is assumed that the constant regions form disulfide-bonds between immunoglobulin heavy chains of the constant regions of each of two polypeptide molecules of said bifunctional polypeptide. Accordingly, preferably an antibody-like structure is formed which closely resembles the structure of an antibody.

Moreover, without being bound by theory it is assumed that this antibody-like structure lends, for example, stability on the bifunctional polypeptide employed in the method of the present invention for detecting methylated DNA. This is because, it is described in the art that proteins fused to a constant region of an antibody may confer a higher stability and half-life of the said protein. In addition, it is believed that the antibody-like structure caused by the intermolecular interaction of the constant regions brings the methyl-DNA-binding domain of one polypeptide of the bifunctional polypeptide used in accordance with the method of the present invention for detecting methylated DNA in close proximity to the methyl-DNA-binding domain of another polypeptide of the present invention employed in the method of the present invention. This allows bivalent interactions between the methyl-DNA-binding protein(s) and methylated DNA. Accordingly, the bifunctional polypeptide described herein is preferably capable of binding to its antigen via two methyl DNA-binding domains which are part of said bifunctional polypeptide. The high affinity binding of the bifunctional polypeptide is, inter alia, also achieved by using preferably methyl-DNA-binding domains of proteins instead of the full-length methyl-DNA-binding protein containing domains for the interaction with other proteins that may, however, disturb or interfere the unique applicability as described herein which are known to specifically bind to methylated DNA, preferably, CpG methylated DNA, rather than to unmethylated DNA. The preferred use of the methyl-DNA-binding domain, moreover, is believed to guarantee that indeed methylated DNA is bound since the detection is direct and not indirect. Most prior art methods can only indirectly detect methylated DNA by PCR.

These properties award the preferred bifunctional polypeptide to be a reliable and easy applicable diagnostic tool which can be employed in the method of the present invention for detecting methylated DNA. Yet, it can also be employed in methods for, inter alia, isolating, purifying enriching methylated DNA even if said DNA is only present in very small amounts, e.g., about more than 10 ng, less than 10 ng, less than 7.5 ng, less than 5 ng, less than 2.5 ng, less than 1000 pg, less than 500 pg, less than 250 pg or about 150 pg as described herein. Accordingly, due to its antibody-like structure the bifunctional polypeptide described herein is a robust molecule rendering it to be applicable, for instance, for various applications including multi-step procedures in a single tube assay as is described herein and in the appended Examples.

The term "contacting" includes every technique which causes that a polypeptide which is capable of binding methylated DNA as is described herein is brought into contact with a sample comprising methylated and/or unmethylated DNA. Preferably, said sample comprising methylated and/or unmethylated DNA is transferred preferably by a pipetting step into the container which is coated with a polypeptide described herein which is capable of binding methylated DNA.

A further advantage of the method of the present invention for detecting methylated DNA is that after the container, preferably a PCR tube has been coated, methylated DNA can be bound by a polypeptide which is capable of binding methylated DNA preferably within 40-50 minutes. Subsequent washing steps which are preferably applied only need preferably about 5 minutes which renders the herein described method for detecting methylated DNA a fast and robust method which can be run in a high-throughput format that can optionally be automated.

The term "detecting" encompasses any technique which is suitable for detecting methylated DNA.

In a preferred embodiment the methylated DNA bound by a polypeptide capable of binding methylated DNA is detected by restriction enzyme digestion, bisulfite sequencing, pyrosequencing or Southern Blot. However, the detection of methylated DNA is not limited to the aforementioned methods but includes all other suitable methods known in the art for detecting methylated DNA such as RDA, microarrays and the like. The term "methylated DNA" encompasses preferably methylated DNA, more preferably, CpG methylated DNA including hemi-methylated DNA or DNA methylated at both strands or single-stranded methylated DNA. The most important example is methylated cytosine that occurs mostly in the context of the dinucleotide CpG, but also in the context of CpNpG- and CpNpN-sequences. In principle, however, other naturally occurring nucleotides may also be methylated.

In an alternative, but also preferred embodiment the methylated DNA bound by a polypeptide capable of binding methylated DNA is detected by an amplification technique, preferably PCR, for example, conventional or real-time PCR including either single or multiplex conventional or real-time PCR using preferably gene-specific primers.

The term "amplification technique" refers to any method that allows the generation of a multitude of identical or essentially identical (i.e. at least 95% more preferred at least 98%, even more preferred at least 99% and most preferred at least 99.5% such as 99.9% identical) nucleic acid molecules or parts thereof. Such methods are well established in the art; see Sambrook et al. "Molecular Cloning, A Laboratory Manual", $2^{nd}$ edition 1989, CSH Press, Cold Spring Harbor. Various PCR techniques, including real-time PCR are reviewed, for example, by Ding, J. Biochem. Mol. Biol. 37 (2004), 1-10.

As mentioned above, a variety of amplification methods are known in the art, all of which are expected to be useful for detecting methylated DNA bound by a polypeptide described herein which is capable of binding methylated DNA in the method of the invention. It is preferred that the detection in step (c) is effected by PCR. PCR is a powerful technique used to amplify DNA millions of fold, by repeated replication of a template, in a short period of time. The process utilizes sets of specific in vitro synthesized oligonucleotides to prime DNA synthesis. The design of the primers is dependent upon the sequences of the DNA that is desired to be analyzed. It is known that the length of a primer results from different parameters (Gillam (1979), Gene 8, 81-97; Innis (1990), PCR Protocols: A guide to methods and applications, Academic Press, San Diego, USA). Preferably, the primer should only hybridize or bind to a specific region of a target nucleotide sequence. The length of a primer that statistically hybridizes only to one region of a target nucleotide sequence can be calculated by the following formula: $(1/4)^x$ (whereby x is the length of the primer). For example a hepta- or octanucleotide would be sufficient to bind statistically only once on a sequence of 37 kb. However, it is known that a primer exactly matching to a complementary template strand must be at least 9 base pairs in length, otherwise no stable-double strand can be generated (Goulian (1973), Biochemistry 12, 2893-2901). It is also envisaged that computer-based algorithms can be used to design primers capable of amplifying the nucleic acid molecules of the invention. Preferably, the primers of the invention are at least 10 nucleotides in length, more preferred at least 12 nucleotides in length, even more preferred at least 15 nucleotides in length, particularly preferred at least 18 nucleotides in length, even more particularly preferred at least 20 nucleotides in length and most preferably at least 25 nucleotides in length. The invention, however, can also be carried out with primers which are shorter or longer.

The PCR technique is carried out through many cycles (usually 20-50) of melting the template at high temperature, allowing the primers to anneal to complimentary sequences within the template and then replicating the template with DNA polymerase. The process has been automated with the use of thermostable DNA polymerases isolated from bacteria that grow in thermal vents in the ocean or hot springs. During the first round of replication a single copy of DNA is converted to two copies and so on resulting in an exponential increase in the number of copies of the sequences targeted by the primers. After just 20 cycles a single copy of DNA is amplified over 2,000,000 fold.

In a preferred embodiment, the aforementioned method further comprises step (d) analyzing the DNA bound by a polypeptide capable of binding to methylated DNA. The analyzis is preferably done by sequencing. Said sequencing is preferably performed by methods known in the art, for example, automated didesoxy-sequencing using fluorescent didesoxy nucleotides according to the method of Sanger (Proc. Natl. Acad. Sci. 74 (1977), 5463-5467). For automated sequencing the DNA to be sequenced is prepared according to methods known in the art and preferably according to the instructions of the kit used for preparing said DNA for sequencing.

Before the present invention is described in detail, it is to be understood that this invention is not limited to the particular methodology, protocols, bacteria, vectors, and reagents etc. described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

CpG islands frequently contain gene promoters and transcription start sites and are usually unmethylated in normal cells. Methylation of CpG-islands is associated with transcriptional repression. In cancer, the methylation of CpG-island promoters leads to the abnormal silencing of tumor-suppressor genes, contributing to the pathogenesis of the disease. As mentioned above, the prior art describes different approaches for the detection of methylated candidate genes which, however, suffer from certain shortcomings. For example, high throughput methods of the prior art may be limited to the detection of single/few CpG residues or may not reliable detect CpG methylated DNA, particularly if only low amounts of DNA can be made subject of an analyzis. To allow a rapid and sensitive detection of the degree of CpG-methylation of candidate genes, the present invention provides means and methods that allow the detection of CpG-methylation, without applying, for example, methylation-sensitive restriction endonucleases or bisulfite-treatment.

In addition to the surprising finding mentioned herein above as regards the method of the present invention for detecting methylated DNA, it was further surprisingly found that binding of methylated DNA and/or fragments thereof to the relatively small surface of containers, preferably PCR-tubes is sufficient to detect preferably a single gene locus within a complex mixture of methylated and/or methylated DNA and/or fragments thereof. Accordingly, it was found that preferably a one-tube assay for detecting methylated DNA termed methyl-binding (MB)-PCR is a reliable and easy applicable diagnostic tool for, inter alia, isolating, purifying, enriching and/or preferably detecting methylated DNA even if said DNA is only present in very small amounts, e.g., about more than 10 ng, less than 10 ng, less than 7.5 ng, less than 5 ng, less than 2.5 ng, less than 1000 pg, less than 500 pg, less than 250 pg or about 150 pg as described herein. Using the methods and kits described herein, it is possible to generate methylation profiles of single or multiple gene loci in for example, human cancer in large numbers of samples.

Briefly, a preferred embodiment of the method of the present invention for detecting methylated DNA is MB-PCR which may work as follows:

A protein with preferably high affinity for methylated DNA, in particular for CpG-methylated DNA, is coated onto the walls of preferably a PCR-cycler compatible reaction container, preferably a tube and used to selectively capture methylated DNA and/or DNA-fragments from preferably a genomic DNA mixture. The retention of a specific DNA and/or DNA-fragment (e.g. a CpG island promoter of a specific gene) can be detected in the same container using PCR (either standard PCR or realtime PCR, single or multiplex). The degree of methylation may be estimated relative to a PCR reaction of the genomic input DNA. Thus, the present invention provides a quick, simple, reliable, robust and extremely sensitive technique allowing the detection of methylated DNA, in particular in tumorous tissue or tumor cells from limited samples.

Figure 1B:
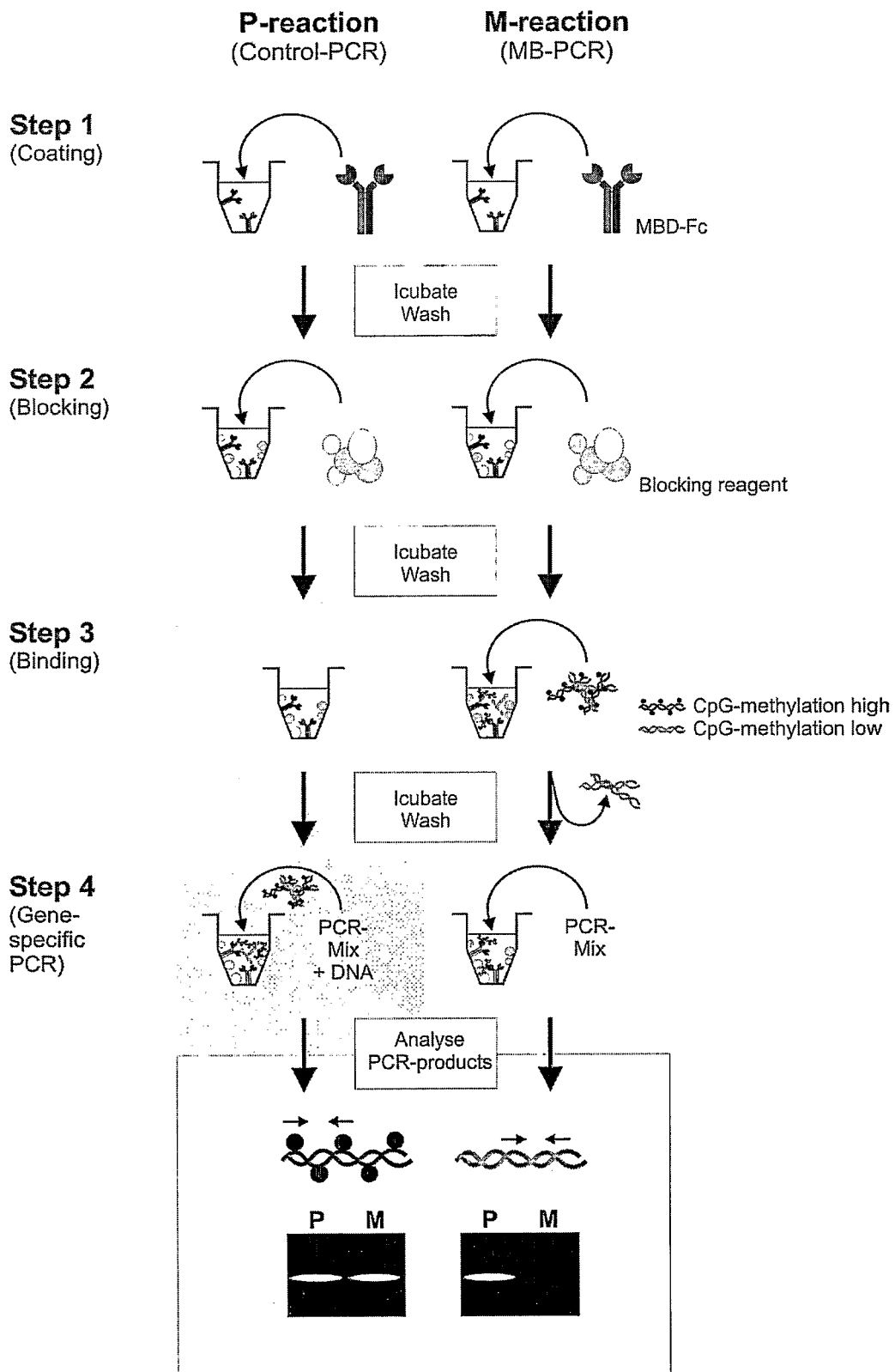

The preferred diagnostic application employing a polypeptide capable of binding methylated DNA is shown in FIG. 1A. FIG. 1B shows the preferred diagnostic application by employing a bifunctional polypeptide which is capable of binding CpG-methylated DNA as described herein. Briefly, in a first step preferably a methyl-CpG-binding polypeptide is preferably added into a coatable PCR-vessel, for example, TopYield Strips from Nunc. In doing so, the polypeptide is preferably coated onto the inner surface of said vessel by techniques known in the art and described herein. In a next step, blocking reagents, e.g., about 5% milk powder are added into the coated PCR vessel. In a further step, preferably DNA-fragments of interest (for example, methylated and/or unmethylated DNA-fragments (the term "CpG-methylation low" used in FIGS. 1A and B comprises and particularly refers to unmethylated DNA)) are added into the coated and blocked PCR vessel. It is believed that the methyl-CpG-binding polypeptide binds specifically to methylated DNA, if present. In a following step, the coated and blocked PCR vessel containing preferably DNA-fragments is incubated and then washed to remove unbound DNA-fragments. Afterwards, a PCR mix including preferably gene-specific primers or, but also preferred, at least two, three, four, five, six, seven etc. pairs of primers for, e.g., multiplex PCR for the gene or genlocus or genloci of interest which is/are suspected to be methylated or unmethylated is added to run preferably, a real time PCR or conventional PCR followed by gel electrophoresis to separate amplification products. Optionally, a control reaction can be performed as is shown in FIG. 1A or 1B as "P-reaction" which is described hereinbelow.

A preferred detailed protocol for MB-PCR is as follows:

Preferably, the PCR tubes are prepared using heat stable TopYield™ Strips (Nunc Cat. No. 248909). Preferably, 50 µl of the a polypeptide described herein, preferably a methyl-CpG-binding polypeptide (diluted at 15 µg/ml in 10 mM Tris/HCl pH 7.5) are added to each well and incubated overnight at 4° C. Preferably, wells are washed three times with 200 µl TBS (20 mM Tris, pH 7.4 containing 170 mM NaCl) and blocked preferably for 3-4 h at RT with 100 µl Blocking Solution (10 mM Tris, pH 7.5 containing 170 mM NaCl, 5% skim milk powder, 5 mM EDTA and 1 µg/ml of each poly d(I/C), poly d(A/T) and poly d(CG)). Preferably, tubes are then washed three times with 200 µl TBST (TBS containing 0.05% Tween-20).

Preferably, 50 µl Binding Buffer (20 mM Tris, pH 7.5 containing 400 mM NaCl, 2 mM $MgCl_2$, 0.5 mM EDTA, and 0.05% Tween-20) are added to each well and preferably 2 µl of digested DNA, preferably genomic DNA digested with MseI in an amount of preferably 5 ng/µl is added to every second well (M-reaction).

Genomic DNA is preferably prepared by using a kit known in the art, for example, using Blood and Cell Culture Midi Kit (Qiagen). The quality of the genomic DNA-preparation is preferably controlled by agarose gel electrophoresis and DNA concentration was preferably determined by UV spectrophotometry. Quantitation of DNA is preferably done by using PicoGreen dsDNA Quantitation Reagent (Molecular Probes).

The wells containing a polypeptide described herein and DNA, preferably DNA-fragments (generated by enzymatic digestion or mechanically fragmented) are incubated on a shaker at preferably RT for preferably 40-50 min. Preferably, tubes were washed two times with 200 µl Binding Buffer and once with 10 mM Tris/HCl pH 8.0.

Next, PCR is preferably carried out directly in the TopYield™ Strips. Preferably, the PCR-Mix (50 µl/well), preferably PCR Master Mix (Promega), contains preferably 10 pmol of each gene-specific primer (synthesized by Metabion). Primer sequences and cycling parameters for specific genes of interest are given in the Example. Of course, any other suitable gene specific or genlocus specific or genloci specific primers can be designed by the person skilled in the art. Moreover, the skilled artisan can readily determine and/or test the PCR parameters most suitable for the primer(s) and gene(s), genlocus/genloci of interest. After adding the PCR-mix, preferably 1 µl Mse I-digested DNA (preferably in an amount of 5 ng/µl) is added to every second other well, that was not previously incubated with DNA-fragments (P-reaction). Preferably, PCR-products are analyzed using agarose gel electrophoresis and the ethidium bromide stained gel was scanned using, for example, a Typhoon 9200 Imager (Amersham/Pharmacia).

Optionally, a control reaction can be performed as is shown in FIG. 1A or 1B as "P-reaction" which is described hereinbelow.

Accordingly, it is envisaged that the method of the present invention is useful for the detection of methylated DNA, preferably CpG-methylated DNA in a sample as described herein below which may include (a) single cell(s). It is also envisaged to be useful for whole cells. "Whole cell" means the genomic context of a whole single cell.

In the following, preferred polypeptides capable of binding methylated DNA are described. Accordingly, a polypeptide used in the methods of the present invention for detecting methylated DNA is preferably selected from the group consisting of (a) a polypeptide belonging to the Methyl-DNA binding protein (MBD) family;
(b) a fragment of the polypeptide of (a), wherein said fragment is capable of binding methylated DNA;
(c) a variant of the polypeptide of (a) or the fragment of (b), wherein in said variant one or more amino acid residues are substituted compared to the polypeptide of (a) or the fragment of (b), and wherein said variant is capable of binding methylated DNA;
(d) a polypeptide which is an anti-methylated DNA antibody or fragment thereof; and
(e) a polypeptide which is at least 70% identical to a polypeptide of any one of (a) to (c) and which is capable of binding methylated DNA.

Of course, it is envisaged that the herein described polypeptides which are capable of detecting methylated DNA are encoded by a nucleic acid molecule. The term "nucleic acid molecule" when used herein encompasses any nucleic acid molecule having a nucleotide sequence of bases comprising purine- and pyrimidine bases which are comprised by said nucleic acid molecule, whereby said bases represent the primary structure of a nucleic acid molecule. Nucleic acid sequences include DNA, cDNA, genomic DNA, RNA, synthetic forms, for example, PNA, and mixed polymers, both sense and antisense strands, or may contain non-natural or derivatized nucleotide bases, as will be readily appreciated by those skilled in the art. The polynucleotide of the present invention encoding a polypeptide which is capable of binding methylated DNA and which is employed in the method of the present invention is preferably composed of any polyribonucleotide or polydeoxyribonucleotide, which may be unmodified RNA or DNA or modified RNA or DNA. For example, the polynucleotide can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. The polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, the term "nucleic acid molecules" embraces chemically, enzymatically, or metabolically modified forms.

In an alternative, but also preferred embodiment, a bifunctional polypeptide (i.e. the MBD protein to be employed in the methods and kits provided herein) capable of binding methylated DNA which is employed in the method of the present invention is encoded by a nucleic acid molecule comprising a nucleotide sequence of the present invention described hereinabove is selected from the group consisting of:

(a) a nucleic acid sequence having the nucleotide sequence shown in SEQ ID NO: 1 (FIG. 7);
(b) a nucleic acid sequence having a nucleotide sequence encoding a polypeptide having the amino acid sequence shown in SEQ ID: NO 2 (FIG. 7);
(c) a nucleic acid sequence having a nucleotide sequence encoding a fragment of a polypeptide having the amino acid sequence shown in SEQ ID: NO 2 (FIG. 7), wherein said fragment comprises at least amino acids 130 to 361 of said polypeptide and which is capable of binding methylated DNA;
(d) a nucleic acid sequence having a nucleotide sequence encoding a variant of a polypeptide encoded by a polynucleotide of any one of (a) to (c), wherein in said variant one or more amino acid residues are substituted compared to said polypeptide, and said variant is capable of binding methylated DNA;
(e) a nucleic acid sequence having a nucleotide sequence which hybridizes with a nucleic acid sequence of any one of (a) to (d) and which is at least 65% identical to the nucleotide sequence of the nucleic acid molecule of (a) and which encodes a polypeptide being capable of binding methylated DNA;
(f) a nucleic acid molecule encoding a polypeptide which is at least 65% identified to a polypeptide encoded by a nucleic acid molecule of (b) and which is capable of binding methylated DNA; and
(g) a nucleic acid sequence having a nucleotide sequence being degenerate to the nucleotide sequence of the polynucleotide of any one of (a) to (f);
or the complementary strand of such a polynucleotide.

The above embodiment relates, accordingly, e.g. to the use of a "MBD-Fc" molecule in the kits and methods provided herein.

As described above, a fragment of a bifunctional polypeptide employed in the method of the present invention for detecting methylated DNA which has the amino acid sequence shown in SEQ ID: NO 2 (FIG. 7) comprises at least amino acids 130 to 361 of the amino acid sequence shown in SEQ ID: NO 2 (FIG. 7). That means that said fragment may comprise in addition to amino acids 130 to 361 which represent the Fc portion, one or more amino acids such that said fragment is capable of binding methylated DNA, preferably, CpG methylated DNA, rather than unmethylated DNA. Accordingly, it is envisaged that said fragment comprises more preferably, at least amino acids 116 to 361 of the amino acid sequence shown in SEQ ID: NO 2 (FIG. 7). Even more preferably, said fragment may comprise at least amino acids 29 to 115 and 130 to 361 of the amino acid sequence shown in SEQ ID: NO 2 (FIG. 7). In a most preferred embodiment, said fragment may comprise at least amino acids 29 to 361. It is generally preferred that the fragments of the a polypeptide described herein are able to bind to methylated DNA, preferably to CpG methylated DNA, rather than unmethylated DNA. This ability can be tested by methods known in the art or preferably by those methods described in the appended Examples.

The present invention preferably also relates to methods, wherein nucleic acid sequences which hybridize to the nucleic acid sequence encoding a polypeptide which is capable of binding methylated DNA are employed. Said hybridizing nucleic acids encode a polypeptide which is capable of binding methylated DNA: Moreover, in the methods of the present invention, nucleic acids are employed which hybridize to the sequences shown in SEQ ID NO: 1 or fragments or variants thereof as described herein (FIG. 7) and which are at least 65% identical to the nucleic acid sequence shown in SEQ ID NO: 1 (FIG. 7) and which preferably encode a bifunctional polypeptide being capable of binding methylated DNA, preferably CpG methylated DNA, rather than unmethylated DNA, wherein said polypeptide is employed in the method of the present invention for detecting methylated DNA. Furthermore, the present invention preferably relates to methods in which nucleic acid sequences encoding a polypeptide are employed which are at least 65%, more preferably 70%, 75%, 80%, 85%, 90%, more preferably 99% identical to a polypeptide as described herein which is capable of binding methylated DNA. It is also preferably envisaged that in the methods of the present invention polypeptides are employed which are at least 65%, more preferably 70%, 75%, 80%, 85%, 90%, more preferably 99% identical to the polypeptide shown in SEQ ID NO:2. The term "hybridizes" as used in accordance with the present invention preferably relates to hybridizations under stringent conditions. The term "hybridizing sequences" preferably refers to sequences which display a sequence identity of at least 65%, even more preferably at least 70%, particularly preferred at least 80%, more particularly preferred at least 90%, even more particularly preferred at least 95% and most preferably at least 97, 98% or 99% identity with a nucleic acid sequence as described above encoding a polypeptide which is capable of binding methylated DNA or a bifunctional polypeptide which is able to bind to methylated DNA, preferably CpG methylated DNA, rather than unmethylated DNA, wherein said polypeptide capable of binding methylated DNA or said bifunctional polypeptide is employed in the method of the present invention for detecting methylated DNA.

Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Such fragments may represent nucleic acid sequences as described herein. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analyzis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementartity between nucleic acid strands has significant effects on the efficiency and strength of hybridization between nucleic acid strands. This is of particular importance in amplification reactions, which depend upon binding between nucleic acids strands.

Moreover, the present invention also relates to methods employed nucleic acid molecules the sequence of which is degenerate in comparison with the sequence of an above-described nucleic acid molecules, wherein such degenerate nucleic acid molecules encode a polypeptide which is capable of binding methylated DNA or which encode a bifunctional polypeptide as described herein and which is employed in the method of the present invention for detecting methylated DNA. When used in accordance with the present invention the term "being degenerate as a result of the genetic code" means that due to the redundancy of the genetic code different nucleotide sequences code for the same amino acid.

Of course, the present invention also envisages the complementary strand to the aforementioned and below mentioned nucleic acid molecules if they may be in a single-stranded form.

Preferably, the nucleic acid molecule encoding a polypeptide which is capable of binding methylated DNA or a bifunctional polypeptide capable of binding methylated DNA and which is/are employed in the method of the present invention may be any type of nucleic acid, e.g. DNA, genomic DNA, cDNA, RNA or PNA (peptide nucleic acid).

For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T_m$) by 8°-20° C., vs. 4°-16° C. for the DNA/DNA 15-mer duplex. Also, the absence of charge groups in PNA means that hybridization can be done at low ionic strengths and reduce possible interference by salt during the analyzis.

The DNA may, for example, be genomic DNA or cDNA. The RNA may be, e.g., mRNA. The nucleic acid molecule may be natural, synthetic or semisynthetic or it may be a derivative, such as peptide nucleic acid (Nielsen, Science 254 (1991), 1497-1500) or phosphorothioates. Furthermore, the nucleic acid molecule may be a recombinantly produced chimeric nucleic acid molecule comprising any of the aforementioned nucleic acid molecules either alone or in combination.

The nucleic acid molecule encoding a polypeptide described herein which is employed in the method of the present invention for detecting methylated DNA is envisaged to be contained in a vector (e.g. a plasmid, cosmid, virus, bacteriophage) which may be transformed into a host cell (a prokaryotic or eukaryotic cell) so as to, inter alia, produce a polypeptide of the present invention which is employed in the method of the present invention. A polypeptide of the invention which is employed in the method of the present invention may be produced by microbiological methods or by transgenic mammals. It is also envisaged that a polypeptide of the invention is recovered from transgenic plants. Alternatively, a polypeptide of the invention may be produced synthetically or semi-synthetically.

For example, chemical synthesis, such as the solid phase procedure described by Houghton Proc. Natl. Acad. Sci. USA (82) (1985), 5131-5135, can be used. Another method is in vitro translation of mRNA. A preferred method involves the recombinant production of protein in host cells as described above. For example, nucleotide acid sequences comprising all or a portion of any one of the nucleotide sequences according to the invention can be synthesized by PCR, inserted into an expression vector, and a host cell transformed with the expression vector. Thereafter, the host cell is cultured to produce the desired polypeptide, which is isolated and purified. Protein isolation and purification can be achieved by any one of several known techniques; for example and without limitation, ion exchange chromatography, gel filtration chromatography and affinity chromatography, high pressure liquid chromatography (HPLC), reversed phase HPLC, preparative disc gel electrophoresis. In addition, cell-free translation systems can be used to produce a polypeptides of the present invention. Suitable cell-free expression systems for use in accordance with the present invention include rabbit reticulocyte lysate, wheat germ extract, canine pancreatic microsomal membranes, *E. coli* S30 extract, and coupled transcription/translation systems such as the TNT-system (Promega). These systems allow the expression of recombinant polypeptides or peptides upon the addition of cloning vectors, DNA fragments, or RNA sequences containing coding regions and appropriate promoter elements. As mentioned supra, protein isolation/purification techniques may require modification of the proteins of the present invention using conventional methods. For example, a histidine tag can be added to the protein to allow purification on a nickel column. Other modifications may cause higher or lower activity, permit higher levels of protein production, or simplify purification of the protein. After production of a polypeptide which is employed in the method of the present invention it may be modified by pegylation, derivatization and the like.

The term "polypeptide belonging to the Methyl-DNA binding protein (MBD)" encompasses a polypeptide which has preferably the structural and/or functional characteristics of the methyl-DNA-binding domain (MBD) of a protein of the MBD family which comprises the proteins MeCP2, MBD1, MBD2, MBD3 and MBD4. Said term also encompasses polypeptides with the capability of binding methylated DNA, including, inter alia, antibodies raised against methylated DNA. Preferably, said antibody is an anti-5-methylcysteine antibody or fragment thereof. Preferably, said fragment is a Fab, F(ab')$_2$, Fv or scFv fragment. The methyl-DNA-binding activity can be tested by methods known in the art. It is preferred that a polypeptide described herein binds methylated DNA either as a monomer or dimer or multivalent molecule as described elsewhere herein. It is preferably capable of binding to highly methylated DNA or low methylated DNA. Preferably, it can bind single methylated CpG pairs. MeCP2, MBD1, MBD2, MBD3 and MBD4 constitute a family of vertebrate proteins that share the methyl-CpG-binding domain. The MBD protein family comprises two subgroups based upon sequences of the known MBDs. The methyl-DNA-binding domain of MBD4 is most similar to that of MeCP2 in primary sequence, while the methyl-DNA-binding domain of MBD1, MBD2 and MBD3 are more similar to each other than to those of either MBD4 or MeCP2. However, the methyl-DNA-binding domains within each protein appear to be related evolutionarily based on the presence of an intron located at a conserved position within all five genes of MeCP2, MBD1, MBD2, MBD3 and MBD4. Yet, the sequence similarity between the members of the MBD family is largely limited to their methyl-DNA-binding domain, although MBD2 and MBD3 are similar and share about 70% of overall identity over most of their length. The greatest divergence occurs at the C-terminus, where MBD3 has 12 consecutive glutamic acid residues.

A protein belonging to the MBD family or fragment thereof, preferably a methyl-DNA-binding domain, useful in accordance with the methods of the present invention can, for example, be identified by using sequence comparisons and/or alignments by employing means and methods known in the art, preferably those described herein and comparing and/or aligning (a) known MBD(s) to/with a sequence suspected to be an MBD.

For example, when a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The percentage identity between two sequences is a function of the number of matching or identical positions shared by the two sequences divided by the number of positions compared×100. For instance, if 6 of 10 of the positions in two sequences are matched or are identical, then the two sequences are 60% identical. By way of example, the DNA sequences CTGACT and CAGGTT share 50% homology (3 of the 6 total positions are matched). Generally, a comparison is made when two sequences are aligned to give maximum homology and/or identity. Such alignment can be provided using, for instance, the method of Needleman, J. Mol. Biol. 48 (1970): 443-453, implemented conveniently by computer programs such as the Align program (DNAstar, Inc.). Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354-352, Nat. Biomed. Res. Foundation, Washington, D.C. (1978).

Preferably, a fragment of a polypeptide described herein and employed in the method of the present invention which is capable of binding methylated DNA, preferably, a methyl-DNA-binding domain or fragment thereof of a polypeptide employed in the method of the present invention, has preferably the structural and/or functional characteristics of a protein belonging to the MBD-family as described herein. Preferably, a fragment of a methyl-DNA-binding protein described herein is able to bind methylated DNA, preferably CpG methylated DNA.

The methyl-DNA-binding domain or fragment thereof of a polypeptide of the present invention which is employed in the method of the present invention is preferably of insect origin, nematode origin, fish origin, amphibian origin, more preferably of vertebrate origin, even more preferably of mammal origin, most preferably of mouse and particularly preferred of human origin.

Preferably, the methyl-DNA-binding domain or fragment thereof of a polypeptide of the present invention which is employed in the method of the present invention possesses a unique alpha-helix/beta-strand sandwich structure with characteristic loops as is shown in FIG. 1 of Ballester and Wolffe, Eur. J. Biochem. 268 (2001), 1-6 and is able to bind methylated DNA.

More preferably, the protein belonging to the MBD family or fragment thereof of a polypeptide of the present invention which is employed in the method of the present invention comprises at least 50, more preferably at least 60, even more preferably at least 70 or at least 80 amino acid residues of the MBDs shown in FIG. 1 of Ballester and Wolffe (2001), loc. cit. and is able to bind methylated DNA.

Even more preferably, the methyl-DNA-binding domain or fragment or variant thereof of a polypeptide of the present invention employed in the method of the present invention shares preferably 50%, 60%, 70%, 80% or 90%, more preferably 95% or 97%, even more preferably 98% and most preferably 99% identity on amino acid level to the MBDs shown in FIG. 1 of Ballester and Wolffe (2001), loc. cit. and is able to bind methylated DNA. Means and methods for determining the identity of sequences, for example, amino acid sequences is described elsewhere herein.

In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., at least 65% identity, preferably, at least 70-95% identity, more preferably at least 95%, 96%, 97%, 98% or 99% identity), when compared and aligned for maximum correspondence over a window of comparison, or over a designated region as measured using a sequence comparison algorithm as known in the art, or by manual alignment and visual inspection. Sequences having, for example, 65% to 95% or greater sequence identity are considered to be substantially identical. Such a definition also applies to the complement of a test sequence. Preferably the described identity exists over a region that is at least about 232 amino acids or 696 nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands.

For example, BLAST2.0, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments. BLAST produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analyzis is much faster than multiple membrane-based hybridizations. In addition, the sensitivity of the computer search can be modified to determine whether any particular match is categorized as exact or similar. The basis of the search is the product score which is defined as:

$$\frac{\%\ \text{sequence identity} \times \%\ \text{maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules.

Most preferably, the methyl-DNA-binding domain or fragment or variant thereof of a polypeptide of the present invention employed in the method of the present invention comprises the methyl-DNA-binding domain of the MBD proteins shown in FIG. 1 of Ballester and Wolffe (2001), loc. cit. or the methyl-DNA-binding domain of the MBD proteins described in Hendrich and Tweedy, Trends Genet. 19 (2003), 269-77 and is able to bind methylated DNA.

Figure 3:
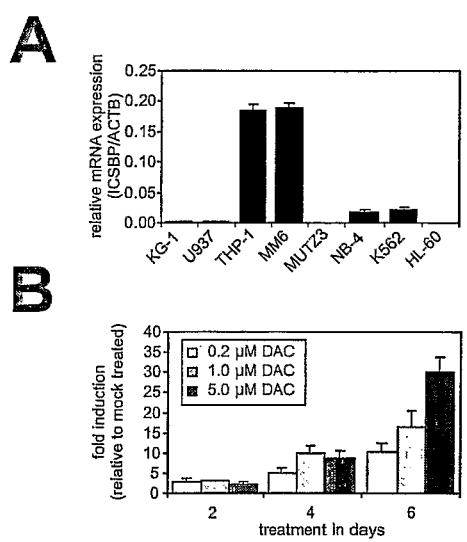

In a particular preferred embodiment of the invention, the methyl-DNA-binding domain of a polypeptide employed in the method of the present invention is that of human MBD2. In a more particular preferred embodiment, the methyl-DNA-binding domain is that of human MBD2 comprising amino acids 144 to 230 of the amino acid sequence having Genbank accession number NM_003927. In a most particular preferred embodiment, the methyl-DNA-binding domain of a polypeptide employed in the method of the present invention comprises the amino acid sequence from position 29 to 115 of the amino acid sequence shown in SEQ ID NO:2 (FIG. 3).

A "variant" of a polypeptide of the present invention which is capable of binding methylated DNA and which is employed in the method of the present invention encompasses a polypeptide wherein one or more amino acid residues are substituted, preferably conservatively substituted compared to said polypeptide and wherein said variant is preferably able to bind to methylated DNA, preferably CpG methylated DNA. Such variants include deletions, insertions, inversions, repeats, and substitutions selected according to general rules known in the art so as have no effect on the activity of a polypeptide of the present invention. For example, guidance concerning how to make phenotypically silent amino acid substitutions is provided in Bowie, Science 247: (1990) 1306-1310, wherein the authors indicate that there are two main strategies for studying the tolerance of an amino acid sequence to change. The first strategy exploits the tolerance of amino acid substitutions by natural selection during the process of evolution. By comparing amino acid sequences in different species, conserved amino acids can be identified, These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein. The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244: (1989) 1081-1085.) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the functions performed by a polypeptide as described herein which is employed in the method of the present invention. Similarity is determined by conserved amino acid substitution. Such substitutions are those that substitute a given amino acid in a polypeptide by another amino acid of like characteristics (e.g., chemical properties). According to Cunningham et al. above, such conservative substitutions are likely to be phenotypically silent. Additional guidance concerning which amino acid changes are likely to be phenotypically silent are found in Bowie, Science 247: (1990) 1306-1310.

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in the Table below.

TABLE IV

| For Amino Acid | Code | Replace with any of: |
| --- | --- | --- |
| Alanine | A | D-Ala, Gly, beta-Ala, L-Cys, D-C₃s |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-As |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine |  | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(0), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Infoliuaties and Genome Projects, Smith, DM., ed., Academic Press, New York, 1993; Informafies Computer Analyzis of Sequence Data, Part 1, Griffin, A. M., and Griffin, H. G., eds., Humana Press, New Jersey, 1994; Sequence Analyzis in Molecular Biology, von Heinje, G., Academie Press, 1987; and Sequence Analyzis Primer, Gribskov, M. and Devereux, eds., M Stockton Press, New York, 1991.

As mentioned herein above, a polypeptide to be used for binding methylated DNA also encompasses preferably an anti-methylated DNA antibody which is preferably an anti-5-methylcytosine antibody or a Fab, F(ab')₂, Fv or scFv fragment thereof. Preferably, said anti-5-methylcytosine antibody specifically binds to methylated DNA, preferably CpG-methylated DNA. The term "specifically" in this context means that said antibody reacts with CpG-methylated DNA, but not with unmethylated DNA and/or DNA methylated at other nucleotides than cytosine and/or DNA methylated at other positions than the C5 atom of cytosine.

Whether the antibody specifically reacts as defined herein above can easily be tested, inter alia, by comparing the binding reaction of said antibody with CpG-methylated DNA and with unmethylated DNA and/or DNA methylated at other nucleotides than cytosine and/or DNA methylated at other positions than the C5 atom of cytosine.

The antibody of the present invention can be, for example, polyclonal or monoclonal. The term "antibody" also comprises derivatives or fragments thereof which still retain the binding specificity such as a Fab, F(ab')₂, Fv or scFv fragment. Techniques for the production of antibodies are well known in the art and described, e.g. in Harlow and Lane "Antibodies, A Laboratory Manual", CSH Press, Cold Spring Harbor, 1988. The present invention furthermore includes chimeric, single chain and humanized antibodies, as well as antibody fragments as mentioned above; see also, for example, Harlow and Lane, loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies to polypeptide(s) of this invention. Also, transgenic animals may be used to express humanized antibodies to polypeptides of this invention. Most preferably, the anti-methylated DNA antibody of this invention is a monoclonal antibody. For the preparation of monoclonal antibodies, any technique which provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Techniques describing the production of single chain antibodies (e.g., U.S. Pat. No. 4,946,778) can be adapted to produce single chain antibodies to immunogenic polypeptides as described above. Accordingly, in context of the present invention, the term "antibody molecule" relates to full immunoglobulin molecules as well as to parts of such immunoglobulin molecules. Furthermore, the term relates, as discussed above, to modified and/or altered antibody molecules, like chimeric and humanized antibodies. The term also relates to monoclonal or polyclonal antibodies as well as to recombinantly or synthetically generated/synthesized antibodies. The term also relates to intact antibodies as well as to antibody fragments thereof, like, separated light and heavy chains, Fab, Fab/c, Fv, Fab', F(ab')2. The term "antibody molecule" also comprises bifunctional antibodies and antibody constructs, like single chain Fvs (scFv) or antibody-fusion proteins. It is also envisaged in context of this invention that the term "antibody" comprises antibody constructs which may be expressed in cells, e.g. antibody constructs which may be transfected and/or transduced via, inter alia, viruses or vectors. Of course, the antibody of the present invention can be coupled, linked or conjugated to detectable substances.

Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to an Fc portion of an antibody (or fragment thereof or indirectly, through an intermediate (such as, for example, a linker known in the art) using techniques known in the art. See, for example, U.S. Pat. No. 4,741,900 for metal ions which can be conjugated to an Fc portion of antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, or $^{99}$Tc. Techniques for conjugating coupling or linked compounds to the Fc portion are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analyzis, Results, And Future Prospective Of The Therapeutic Use Of Radiolabeled Antibody In Cancer Therapy", in Monoelonal Antibodies For Cancer Detection And Therapy, Baldwin et al. (eds.), pp. 303-16 (Academic Press 1985), and Thorpe, Immunol. Rev., 119-158.

In a preferred embodiment of the present invention, a polypeptide as described herein which is used in the method of the present invention is fused at its N- and/or C-terminus to a heterologous polypeptide for detecting methylated DNA which is preferably selected from the group consisting of a HA-tag, myc6-tag, FLAG-tag, STREP-tag, STREP II-tag, TAP-tag, HAT-tag, chitin-binding domain (CBD), maltose-binding protein, His6-tag, Glutathione-S-transferase (GST) tag, Intein-tag, Streptavidin-binding protein (SBP) tag and a Fc-portion of an antibody. A "tag" is an amino acid sequence which is homologous or heterologous to an amino acid sequence sequence to which it is fused. Said tag may, inter alia, facilitate purification of a protein or facilitate detection of said protein to which it is fused. The fusion refers to a co-linear linkage and results in a translation fusion. In an also further preferred embodiment a polypeptide of the present invention which is capable of binding methylated DNA is fused to a heterologous polypeptide and optionally comprises an additional linker between the N- and/or C-terminus of said polypeptide and said heterologous polypeptide. Said linker is preferably a flexible linker. Preferably, it comprises plural, hydrophilic, peptide-bonded amino acids. Optionally, the linker comprises a protease cleavage site which allows to cut off the heterologous polypeptide fused to a polypeptide of the present invention, if desirable. Protease cleavage sites are, for example, a thrombin cleavage site.

Preferably, said linker comprises a plurality of glycine, alanine, aspartate, glutamate, proline, isoleucine and/or arginine residues. It is further preferred that said polypeptide linker comprises a plurality of consecutive copies of an amino acid sequence. Usually, the polypeptide linker comprises 1 to 20, preferably 1 to 19, 1 to 18, 1 to 17, 1 to 16 or 1 to 15 amino acids although polypeptide linkers of more than 20 amino acids may work as well.

Preferably, said Fc protein of an antibody comprises preferably at least a portion of the constant region of an immunoglobulin heavy chain molecule. The Fc region is preferably limited to the constant domain hinge region and the $C_H2$ and $C_H3$ domains. The Fc region in a polypeptide of the present invention which is capable of binding methylated DNA and which is employed in the method of the present invention can also be limited to a portion of the hinge region, the portion being capable of forming intermolecular disulfide bridges, and the $C_H2$ and $C_H3$ domains, or functional equivalents thereof.

Alternatively, it is also preferred that the Fc portion comprises at least so many $C_H$ regions which are required such that a polypeptide of the present invention capable of binding methylated DNA has still the properties of a polypeptide described hereinabove, in particular the properties of the polypeptide used in the appended Examples.

In another alternative, it is also preferred that said constant region may contain one or more amino acid substitutions when compared to constant regions known in the art. Preferably it contains 1 to 100, 1 to 90, 1 to 80, 1 to 70, 1 to 60, 1 to 50, 1 to 40, 1 to 30 or 1 to 20, more preferably 1 to 10, even more preferably 1 to 9, 1 to 8, 1 to 7 or 1 to 6 and most preferably 1 to 5, 1 to 4, 1 to 3 or 2 or 1 substitution(s). The comparison is preferably done as is known in the art or, more preferably, as described elsewhere herein.

Alternatively, said constant region comprises preferably at least the $C_H1$ region, more preferably the $C_H1$ and $C_H2$ regions and most preferably the $C_H1$, $C_H2$ and $C_H3$ region. As is known in the art, the constant region of an antibody contains two immunoglobulin heavy chains which harbour three characteristic immunoglobulin domains composed of about 110 amino acids, wherein the two immunoglobulin heavy chains are covalently linked via disulfide bonds.

It is also envisaged that the constant region could preferably be of chicken or duck origin. Yet, preferably, the constant region is of the IgM, IgA, IgD or IgE isotype and more preferably it is of the IgG isotype, most preferably of the IgG1 isotype. Preferably, the aforementioned isotypes are of vertebrate origin, more preferably of mammal origin, even more preferably of mouse, rat, goat, horse, donkey, camel or chimpanzee origin and most preferably of human origin. Preferably, said IgG isotype is of class IgG1, IgG2, IgG3, IgG4 and said IgA isotype is of class IgA1, IgA2.

In a further preferred embodiment of the present invention a polypeptide used in the method of the present invention is a fusion protein between the methyl-DNA binding domain of the MBD2 protein and the Fc portion of an antibody as disclosed herein. Optionally the preferred fusion protein comprises a linker polypeptide as described herein, wherein said linker polypeptide is preferably located between the methyl-DNA binding domain of MBD2 and the Fc portion of an antibody.

The herein described heterologous polypeptide fused to a polypeptide used in the method of the present invention facilitates binding and/or attachment of a polypeptide used in the method of the present inventions to a container or solid support including, but not limited to, glass, cellulose, polyacrylamide, nylon, polycarbonate, polystyrene, polyvinyl chloride or polypropylene or the like. Preferably, said container is a PCR-tube composed of polycarbonate and more preferably it is a heat stable TopYield™ strip from Nunc Cat. No. 248909. Said PCR-tube or strip may be in the format of a 96-well, 384-well or 1024-well plate. Accordingly, the method of the present invention is suitable for high-through put applications which can be automated since the method of the present invention can be performed as so-called "one tube—one assay".

In a preferred embodiment, the container or solid support, preferably a PCR-tube or stripe is coated directly or indirectly with a polypeptide used in the method of the present invention: for example, coating would be achieved directly by using a biotinylated polypeptide of the present invention and a streptavidin coated container, preferably a PCR-tube. However, any other technique known in the art for coating a container with a polypeptide are contemplated by the present invention. Indirect coating can preferably be achieved by an antibody coated onto the surface of said container and which is capable to specifically bind either a polypeptide of the present invention which is capable of binding methylated DNA or specifically binding the heterologous polypeptide preferably fused to said polypeptide capable of binding methylated DNA or specifically binding the anti-methylated DNA antibody of the present invention. In fact, said container is indirectly coated with a polypeptide of the present invention which is capable of binding methylated DNA.

Coating of the container as described herein may be achieved, for example, by coating said container with an agent which is suitable to interact with the heterologous polypeptide fused to a polypeptide of the present invention which is capable of binding methylated DNA. For example, said container may be coated with glutathione and, accordingly, a GST-tagged polypeptide of the present invention is bound by glutathione which results in coating of said container with a polypeptide to be employed in the method of the present invention. Preferably, coating of the container occurs due to the property of the plastic out of which the preferred container described herein is built. Accordingly, when a polypeptide of the present invention is brought in contact with a container of the present invention, said polypeptide coates said container.

As mentioned herein, the method of the present invention allows the detection of methylated DNA of, preferably, a single gene locus which renders it a suitable diagnostic tool for, inter alia, detecting methylated DNA from more than 15 µg, less than 15 µg, less than 10 µg, less than 10 ng, 7.5 ng, 5 ng, 2.5 ng, 1 ng, 0.5 ng, 0.25 ng, or about 150 pg. By the term biological sample obtained from a subject or an individual, cell line, tissue culture, or other source containing polynucleotides or polypeptides or portions thereof. As indicated, biological samples include body fluids (such as blood, sera, plasma, urine, synovial fluid and spinal fluid) and tissue sources found to express the polynucleotides of the present invention. Methods for obtaining tissue biopsies and body fluids from mammals are well known in the art. A biological sample which includes genomic DNA, mRNA or proteins is preferred as a source.

Without being bound by theory, it is believed that methylation of CpG dinucleotides correlates with stable transcriptional repression and presumably leads to the fact that large parts of the non-coding genome and potentially harmful sequences are not transcribed. A global DNA hypomethylation has been described for almost all kinds of tumours. In tumour tissue, the content in 5-methylcytosine is reduced compared to normal tissue with the major share of demethylation events being found in repetitive satellite sequences or in centromer regions of the chromosomes. However, in single cases, the demethylation and activation of proto-oncogenes such as, e.g., bcl-2 or c-myc have also been described (Costello, J. Med. Genet. 38 (2001), 285-303). CpG islands in general exert gene regulatory functions. This is why a change in the status of methylation correlates mostly directly with a change in the transcriptional activity of the locus concerned (Robertson (1999); Herman (2003); Esteller (2002); Momparler (2003); Plass (2002), all loc. cit.). Most CpG islands are present in unmethylated form in normal cells. In certain situations, CpG islands can, however, also be methylated in gene regulatory events. The majority of CpG islands of the inactivated X-chromosome of a female cell are, for example, methylated (Goto, Microbiol. Mol. Biol. Rev. 62 (1998), 362-378). CpG islands can be methylated also in the course of normal aging processes (Issa, Clin. Immunol. 109 (2003), 103-108).

It is in particular in tumours that CpG islands which are normally not methylated can be present in a hypermethylated form. In many cases, genes affected by the hypermethylation encode proteins which counteract the growth of a tumour such as, e.g., tumour suppressor genes. Examples of genes for which it could be shown that they can be inactivated in tumours through the epigenetic mechanism of hypermethylation are described herein above. Reasons for the tumour-specific hypermethylation are almost unknown. Interestingly, certain kinds of tumours seem to have their own hypermethylation profiles. It could be shown in larger comparative studies that hypermethylation is not evenly distributed but that it occurs depending on the tumour. In cases of leukaemia, mostly other genes are hypermethylated compared to, for instance, colon carcinomas or gliomas. Thus, hypermethylation could be useful for classifying tumours (Esteller, Cancer Res. 61 (2001), 3225-3229; Costello, Nat. Genet. 24 (2000), 132-138).

Thus, it is believed that epigenetic effects such as hypo- and/or hypermethylation are correlated with cancers, tumors and/or metastatis.

The subject of the present invention from which the sample is obtained for detecting methylated DNA is suspected to have hypo- and/or hypermethylated genloci. Said hypo- and/or hypermethylated genloci are indicative of a cancer, tumor or metastasis. The tumor or cancer can be any possible type of tumor or cancer. Examples are skin, breast, brain, cervical carcinomas, testicular carcinomas, head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukaemia, a paraneoplastic syndrome, a peritoneal carcinomastosis, a immunosuppression-related malignancy and/or metastatic cancer etc. The tumor cells may, e.g., be derived from: head and neck, comprising tumors of the nasal cavity, paranasal sinuses, nasopharynx, oral cavity, oropharynx, larynx, hypopharynx, salivary glands and paragangliomas, a cancer of the lung, comprising non-small cell lung cancer, small cell lung cancer, a cancer of the mediastinum, a cancer of the gastrointestinal tract, comprising cancer of the oesophagus, stomach, pancreas, liver, biliary tree, small intestine, colon, rectum and anal region, a cancer of the genitourinary system, comprising cancer of the kidney, urethra, bladder, prostate, urethra, penis and testis, a gynaecologic cancer, comprising cancer of the cervix, vagina, vulva, uterine body, gestational trophoblastic diseases, ovarian, fallopian tube, peritoneal, a cancer of the breast, a cancer of the endocrine system, comprising a tumor of the thyroid, parathyroid, adrenal cortex, pancreatic endocrine tumors, carcinoid tumor and carcinoid syndrome, multiple endocrine neoplasias, a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of tumors, rhabdomyosarcoma, a lymphoma, comprising non-Hodgkin's lymphomas, cutaneous T-cell lymphomas, primary central nervous system lymphoma, and Hodgkin's disease, a leukaemia, comprising acute leukemias, chronic myelogenous and lymphocytic leukemias, plasma cell neoplasms and myelodysplastic syndromes, a paraneoplastic syndrome, a cancer of unknown primary site, a peritoneal carcinomastosis, a immunosuppression-related malignancy, comprising AIDS-related malignancies, comprising Kaposi's sarcoma, AIDS-associated lymphomas, AIDS-associated primary central nervous system lymphoma, AIDS-associated Hodgkin's disease and AIDS-associated anogenital cancers, and transplantation-related malignancies, a metastatic cancer to the liver, metastatic cancer to the bone, malignant pleural and pericardial effusions and malignant ascites. It is mostly preferred that said cancer or tumorous disease is cancer of the head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukemia, a paraneoplastic syndrome, a peritoneal carcinomastosis, a immunosuppression-related malignancy and/or metastatic cancer. Preferred tumors are AML, plasmacytoma or CLL.

As mentioned herein, the present invention provides a method for detecting methylated DNA, preferably CpG-methylated DNA fragments in a single-tube assay comprising the following steps: binding of genomic DNA to polypeptide which is capable of binding methylated DNA, preferably a methyl-CpG-binding protein, coated onto to the inner surface of a container, preferably a PCR-tube, washing off unbound (unmethylated) DNA-fragments and preferably directly applying gene-specific PCR to detect the enrichment of methylated DNA. Since the method of the present invention is robust, fast and is an easy applicable and reliable diagnostic tool for detecting methylated DNA due to the "one reaction container for all steps", the method of the present invention may be applicable to high through put formats which may be made subject of automation. The method of the present invention allows thus an easy and highly sensitive detection of CpG methylation of preferably (a) single gene locus/loci. Since methylation patterns of tumors and/or cancers appear to develop into a valuable diagnostic parameter, it is preferred to provide a kit comprising all means for carrying out the method of the present invention.

Accordingly, the present invention relates to a kit comprising for detecting methylated DNA according to the method of the present invention comprising
(a) a polypeptide capable of binding methylated DNA as described herein;
(b) a container which can be coated with said polypeptide; and
(c) means for coating said container; and
(d) means for detecting methylated DNA.

The embodiments disclosed in connection with the method of the present invention apply, mutatis mutandis, to the kit of the present invention.

Advantageously, the kit of the present invention further comprises, optionally (a) reaction buffer(s), storage solutions, wash solutions and/or remaining reagents or materials required for the conduction of scientific or diagnostic assays or the like as described herein. Furthermore, parts of the kit of the invention can be packaged individually in vials or bottles or in combination in containers or multicontainer units. The kit of the present invention may be advantageously used, inter alia, for carrying out the method for detecting methylated DNA as described herein and/or it could be employed in a variety of applications referred herein, e.g., as diagnostic kits, as research tools or therapeutic tools. Additionally, the kit of the invention may contain means for detection suitable for scientific, medical and/or diagnostic purposes. The manufacture of the kits follows preferably standard procedures which are known to the person skilled in the art. The kit of the present invention is preferably useful in a "single-tube" assay as provided herein.

"Means for coating" of the container of the present invention are all agents suitable for coating said container with a polypeptide of the present invention, for example, cross-linking agents or avidin or glutathione or the like. Thus, basically, every agent which is suitable to interact with the heterologous polypeptide fused to a polypeptide of the present invention which is capable of binding methylated DNA. Preferably, the kit of the present invention comprises pre-coated containers, preferably PCR-tubes.

The term "means for detecting methylated DNA" encompasses all agents necessary to carry out the detection methods for methylated DNA as described herein above. In a more preferred embodiment, said kit comprises an instruction manual how to carry out detection of methylated DNA according to the method of the present invention.

The figures show:

FIG. 1: Outline of Methyl-binding (MB)-PCR. (A) The major steps of the MB-PCR procedure are illustrated. MB-PCR comprises of two separate reactions, the control-PCR reaction (P-reaction) which amplifies a candidate locus directly from a genomic template, and the methyl-CpG-binding-PCR reaction which amplifies the candidate locus from the template DNA that was previously bound by a methyl-CpG-binding polypeptide in the reaction vessel (M-reaction). In the first step, the inner walls of both reaction vessels are coated with a methyl-binding polypeptide and subsequently saturated using blocking reagents (step 2). The template DNA (genomic DNA restricted with Mse I or similar enzymes) is then added to one tube (M-reaction) and allowed to bind (step 3). In the last step, the PCR reaction mix is added directly into both tubes and 50% of template DNA previously used for the M-reaction is added to the P-reaction. After gene-specific PCR, products may be analyzed, e.g. by agarose gel electrophoresis. The term "CpG-methylation low" used in FIGS. 1A and B comprises and particularly refers to unmethylated DNA (B) Schematic representation of the MB-PCR procedure using a recombinant methyl-binding polypeptide MBD-Fc described herein above.

FIG. 2: Detecting CpG methylation in leukaemia cell lines at three CpG-island promoters by MB-PCR. (A) Shown are: the position of CpG-dinucleotides, Mse I-restriction sites, first exons and positions of primers used to detect promoter fragments of ICSBP, ESR1, and CDKN2B (p15$^{INK4b}$). (B) Representative MB-PCR results of the indicated promoters for eight different leukaemia cell lines. The P-reaction directly amplifies the genomic DNA, whereas the M-reaction only amplifies CpG-methylated DNA fragments.

FIG. 3: Methylation of the ICSBP promoter inversely correlates with ICSBP expression in leukaemia cell lines. (A) Transcription levels of ICSBP were determined by LightCycler real time PCR relative to the housekeeping gene ACTB. (B) U937 cells, treated with Decitabine (DAC) for the indicated time periods were analyzed for ICSBP expression. Results were normalized to ACTB expression. Data represent mean values±SD of two independent LightCycler analyses.

Figure 4:
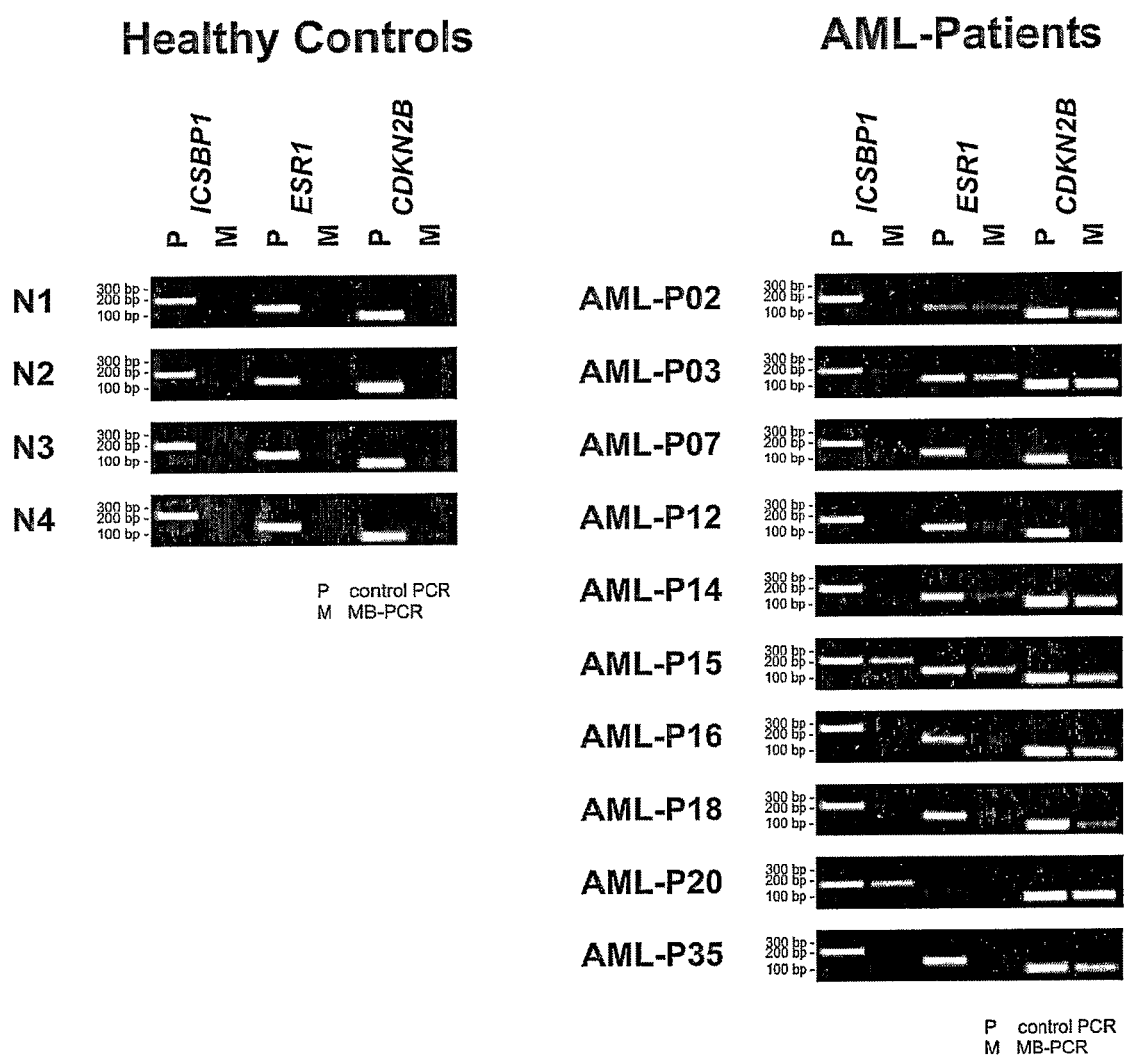

FIG. 4: Detection of aberrant CpG methylation in AML cells. Representative MB-PCRs for ESR1, CDKN2B (p15$^{INK4b}$), and ICSBP promoters of several healthy donors and AML patients.

Figure 5:
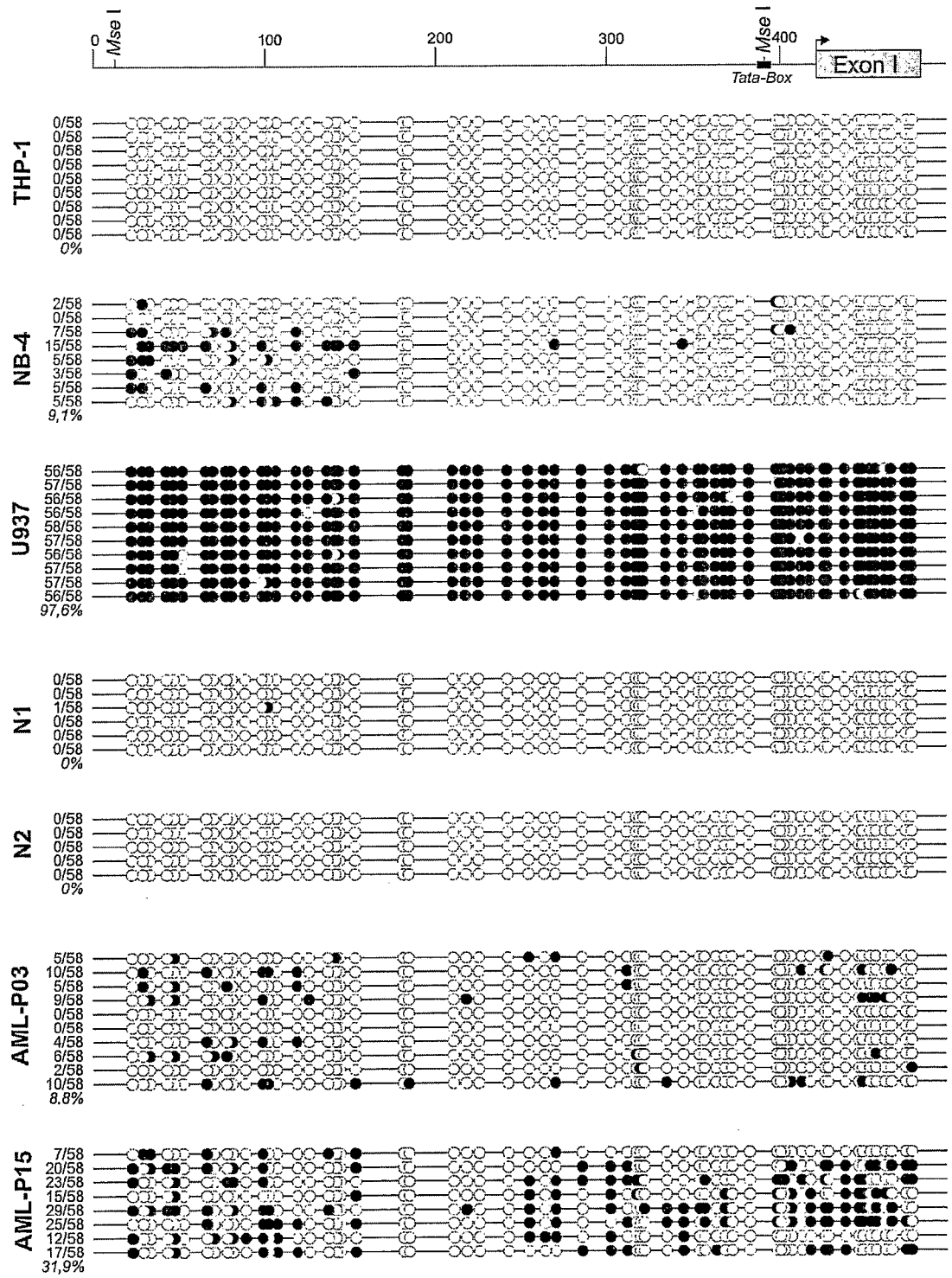

FIG. 5: MB-PCR of the ICSBP promoter correlates with the results obtained by bisulfite sequencing. Genomic DNA derived from cell lines as well as cells of selected healthy donors and AML patients was treated with bisulfite. The indicated region of the ICSBP-gene was amplified and cloned. Several independent inserts were sequenced and results are presented schematically. Circles mark the position of CpG-dinucleotides (empty: unmethylated; filled: methylated).

FIG. 6: Sensitivity of MB-PCR. (A) MB-PCRs for ESR1, CDKN2B (p15$^{INK4b}$), and ICSBP promoters from mixtures of DNA from a healthy donor (unmethylated) DNA and DNA from the cell line KG-1 (methylated in all three loci). (B) DNA from three cell lines was subjected to MB-PCR using the indicated amounts of DNA for the M-reaction (or half of the indicated amount for the P-reaction). With decreasing amounts of DNA, the number of amplification cycles during PCR (given in parenthesis) was increased. Also shown is a sample that did not include DNA ($H_2O$).

FIG. 7: FIG. 7 shows the nucleotide sequence of plasmid pMTBip/MBD2-Fc and the protein sequence (in bold) of the MBD2-Fc bifunctional protein which is encoded by plasmid pMTBip/MBD2-Fc.

The amino acid sequence of the MBD2-Fc bifunctional protein has the following features.

AA 1-28 (nt 851-934): *Drosophila* BiP secretion signal (leader peptide from pMT/Bip/V5-His vector):
AA 29-115 (nt 935-1196): AA 144-230 of human MBD2
AA 116-129 (nt 1196-1237): Flexible Linker (AAAD-PIEGRGGGG)
AA 130-361 (1238-1933): AA99-330 of human IGHG1

FIG. 8: MB-PCR detects methylation of CpG-island promoters (A) Schematic presentation of the detected MseI-fragments (indicated as grey boxes) of ESR1, CDKN2B (p15INK4b), ICSBP, ETV3 and DDX20. The position of CpG-dinucleotides, MseI-restriction sites, transcription start site, first exon and relative position of primers are marked. (B) Shown are representative MB-PCR results of normal (unmethylated) and in vitro methylated genomic DNA for the indicated promoters. The P-reaction directly amplifies the genomic DNA, whereas the M-reaction only amplifies CpG-methylated DNA fragments.

Figure 9:
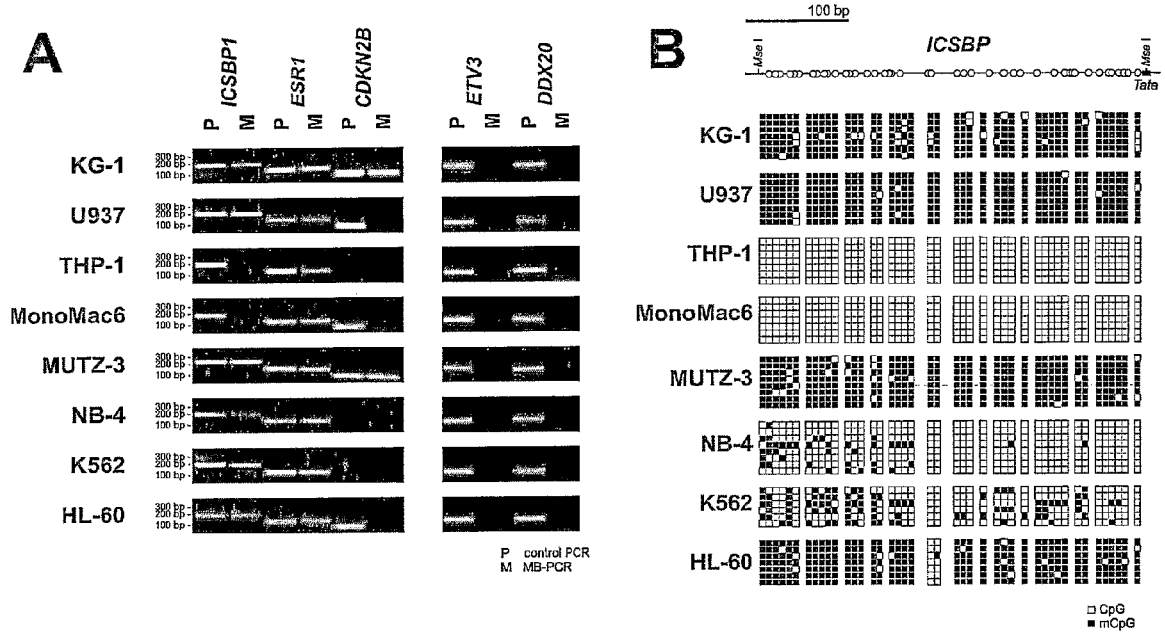

FIG. 9: Detecting CpG methylation in leukaemia cell lines by MB-PCR. (A) Shown are representative MB-PCR results of eight different leukaemia cell lines for the indicated promoters. (B) Genomic DNA from the same cell lines was analyzed by bisulfite sequencing. The indicated region of the ICSBP gene was amplified and cloned. Several independent inserts were sequenced and results are presented schematically. Squares mark the position of CpG-dinucleotides (empty: unmethylated; filled: methylated).

Figure 10:
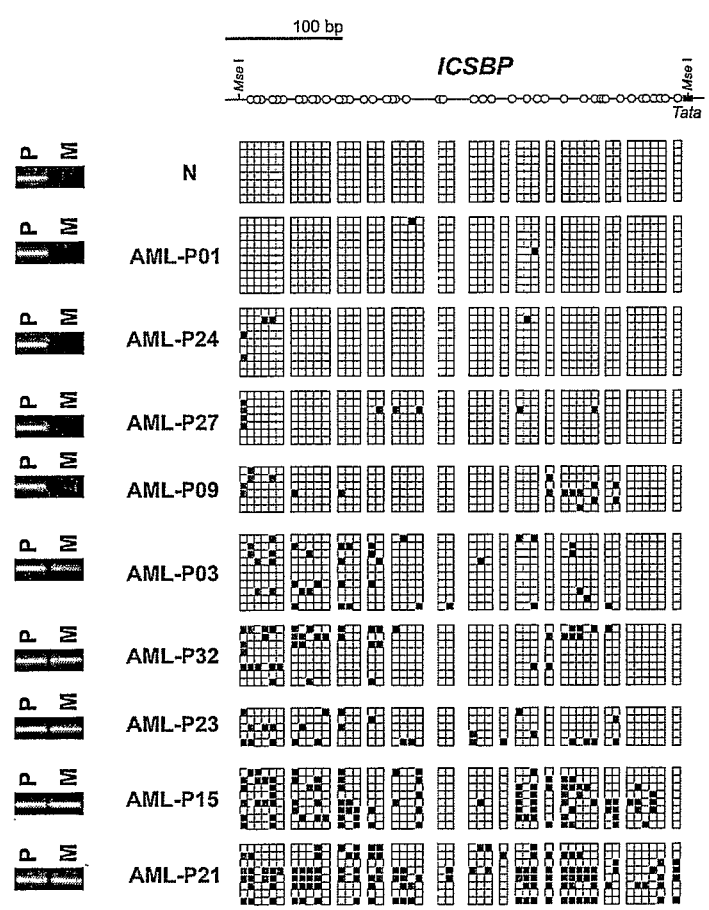

FIG. 10: Detection of aberrant CpG methylation in primary AML blasts. Two for the ICSBP promoter of one representative healthy donor (N) and nine AML patients are shown together with corresponding sequencing results. (Results of bisulfite sequencing are presented as described in FIG. 9.)

A better understanding of the present invention and of its many advantages will be seen from the following examples, offered for illustrative purposes only, and are not intended to limit the scope of the present invention in any way.

EXAMPLE 1

Single-tube Assay for the Detection of CpG-methylated DNA-fragments Using Methyl-binding Polymerase Chain Reaction (MB-PCR)

This method uses an approach similar to ELISAs. A protein with high affinity for CpG-methylated DNA is coated onto the walls of a PCR-cycler compatible reaction vessel and used to selectively capture strongly methylated DNA-fragments from a genomic DNA mixture. The retention of a specific DNA-fragment (e.g. a CpG island promoter of a specific gene) can be detected in the same tube using PCR (either standard PCR or realtime PCR, single or multiplex). The degree of methylation may be estimated relative to a PCR reaction of the genomic input DNA. FIG. 1 shows a schematic representation of MB-PCR.

1. Cells, Patient Samples, DNA Preparation and Fragmentation

Cells

Peripheral blood mononuclear cells (MNC) were separated by leukapheresis of healthy donors, followed by density gradient centrifugation over Ficoll/Hypaque. Monocytes were isolated from MNC by countercurrent centrifugal elutriation in a J6ME centrifuge (Beckman, München, Germany) as described in Krause, J. Leukoc. Biol. 60 (1996), 540-545. *Drosophila* S2 cells were obtained from ATTC and cultured in Insect-Xpress medium (Bio Whittaker) containing 10% fetal calf serum (FCS; PAA) in an incubator at 21° C. The human myeloid leukaemia cell lines THP-1, NB-4, KG-1, K562, HL-60 and U937 were grown in RPMI 1640 medium supplemented with 10% FCS. The human myeloid leukaemia cell line Mono Mac 6 was grown RPMI 1640 medium plus 10% FCS and 1% OPI media supplement (Sigma). The human myeloid leukaemia cell line MUTZ-3 was maintained in αMEM plus 20% FCS and 10 ng/ml stem cell factor. For DNA-demethylation, U937 cells were treated with the indicated amounts of Decitabine (2-deoxy-5'-azacytidine, Sigma) for several days.

Patient Samples

Fresh peripheral blood samples and bone marrow specimens from 35 patients with newly diagnosed and untreated de novo or secondary AML were used for the study. All patients were treated according to the protocol AMLCG-2000 of the German AML Cooperative Group. The study was approved by the Institutional Ethics Committee, and written informed consent was obtained from each patient before entering the study.

DNA Preparation and Fragmentation

Genomic DNA from various cellular sources, including the cell lines described herein (e.g. KG1, U937, and THP-1), normal human monocytes (healthy donor) and frozen blast cells from a patient with AML were prepared using Blood and Cell Culture Midi Kit (Qiagen). Quality of the genomic DNA-preparation was controlled by agarose gel electrophoresis and DNA concentration was determined by UV spectrophotometry. Genomic DNA was digested with Mse I (NEB) and finally quantified using PicoGreen dsDNA Quantitation Reagent (Molecular Probes). Where indicated. DNA was in vitro methylated using Sss I methylase (NEB).

2. Generation of a Recombinant Methyl-CpG-binding Polypeptide

A cDNA corresponding to the methyl-CpG binding domain (MBD) of human MBD2 (Genbank acc. no. NM_003927; AA 144-230) was PCR-amplified from reverse transcribed human primary macrophage total RNA using primers MBD2-Nhe_S (5'-AGA TGC TAG CAC GGA GAG CGG GAA GAG G-3') (SEQ ID NO: 4) and MBD2-Not_AS (5'-ATC ACG CGG CCG CCA GAG GAT CGT TTC GCA GTC TC-3') (SEQ ID NO: 5) and Herculase DNA Polymerase (Stratagene). Cycling parameters were: 95° C., 3 min denaturation; 95° C., 20 s, 65° C., 20 s, 72° C., 80s amplification for 34 cycles; 72° C., 5 min final extension. The PCR-product was precipitated, digested with Not I/Nhe I, cloned into NotI/NheI-sites of Signal pIg plus vector (Ingenius, R&D Systems) and sequence verified resulting in pIg/MBD2-Fc (eukaryotic expression vector). To clone pMTBip/MBD2-Fc for recombinant expression in *Drosophila* S2 cells, the Apa I/Nhe I-fragment of pIg/MBD2-Fc containing the MBD of human MBD2 fused to the Fc-tail of human IgG1 was subcloned into Apa I/Spe I-sites of pMTBiP/V5-His B (Invitrogen).

*Drosophila* S2 cells were obtained from ATTC and cultured in Insect-Xpress medium (Bio Whittaker) containing 10% FCS (PM) in an incubator at 21° C. $4 \times 10^6$ *Drosophila* S2 cells/60 mm cell culture dish were transfected with a mixture of 1.5 µg pMTBip/MBD2-Fc and 0.3 µg pCoHygro (Invitrogen) using Effectene transfection reagent (Qiagen) according to the manufacturers protocol. On day three, transfected cells were harvested, washed and replated in selection medium (Insect-Xpress) containing 10% FCS and 300 µg/ml Hygromycin (BD Biosciences). Selection medium was replaced every 4-5 days for five weeks. The pool of stably transfected *Drosophila* S2 cells was expanded. For large scale production of the methyl-CpG binding polypeptide MBD-Fc, $1-5 \times 10^8$ cells were cultured in 100-200 ml Insect-Xpress without FCS (optional: 300 µg/ml Hygromycin) in 2000 ml roller bottles for two days before the addition of 0.5 mM $CuSO_4$. Medium was harvested every 4-7 days and cells were replated medium plus $CuSO_4$ for further protein production. Cell culture supernatants were combined, dialysed against TBS (pH 7.4) and purified using a protein A column. The MBD-Fc containing fractions were combined and dialysed against TBS (pH 7.4). The stably transfected *Drosophila* S2 cells produced 3-5 mg recombinant MBD2-Fc protein per litre cell culture supernatant. The sequence and features of the MBD-Fc protein are shown in FIG. 7.

3. Preparation of MB-PCR Tubes

50 µl of the recombinant MBD2-Fc protein comprising the methyl-CpG binding domain (MBD) of human methyl-CpG-binding domain 2 (MBD2), a flexible linker polypeptide and the Fc portion of human IgG1 (diluted at 15 µg/ml in 10 mM Tris/HCl pH 7.5) were added to each well of heat stable TopYield™ Strips (Nunc Cat. No. 248909) and incubated overnight at 4° C. Wells were washed three times with 200 µl TBS (20 mM Tris, pH 7.4 containing 170 mM NaCl) and blocked at RT for 3-4 h with 100 µl Blocking Solution (10 mM Tris, pH 7.5 containing 170 mM NaCl, 5% skim milk powder, 5 mM EDTA and 1 µg/ml of each poly d(I/C), poly d(A/T) and poly d(CG), all from Amersham). Tubes were washed three times with 200 µl TBST (TBS containing 0.05% Tween-20).

4. Binding of Methylated DNA Fragments

50 µl Binding Buffer (20 mM Tris, pH 7.5 containing 400 mM NaCl, 2 mM $MgCl_2$, 0.5 mM EDTA, and 0.05% Tween-20) were added to each well and 2 µl Mse I-digested DNA (5 ng/µl) was added to every second well (M-reaction). Wells were incubated on a shaker at RT for 40-50 min. Tubes were washed two times with 200 µl Binding Buffer and once with 10 mM Tris/HCl pH 8.0.

5. Detection of Methylated DNA Fragments

PCR was carried out directly in the treated and washed TopYield™ Strips. The PCR-mix (PCR Master Mix (Promega); 50 µl-reactions/well) included 10 pmol of each gene-specific primer (synthesized by Metabion). Primer sequences were P15 S (5'-GGC TCA GCT TCA TTA CCC TCC-3') (SEQ ID NO: 6), P15 AS (5'-AAA GCC CGG AGC TAA CGA C-3') (SEQ ID NO: 7), ESR1 S (5'-GAC TGC ACT TGC TCC CGT C-3') (SEQ ID NO: 8), ESR1 AS (5'-AAG AGC ACA GCC CGA GGT TAG-3') (SEQ ID NO: 9), ICSBP S (5'-CGG AAT TCC TGG GAA AGC C-3') (SEQ ID NO: 10), ICSBP AS (5'-TTC CGA GAA ATC ACT TTC CCG-3') (SEQ ID NO: 11), METS S (5'-AAT TGC GTC TGA AGT CTG CGG-3'), (SEQ ID NO. 12), METS AS (5'-TCC CAC ACA ACA GAG AGG CG-3') (SEQ ID NO. 13), DP103 S (5'-GCT GTT AGT CCA GTT CCA GGT TCC-3') (SEQ ID NO. 14), DP103 AS (5'-GTG CM CCA CAT TTA TCT CCG G-3') (SEQ ID NO: 15).

After adding the PCR-mix, 1 µl Mse I-digested DNA (5 ng/µl) was added to every second other well, that was not previously incubated with DNA-fragments (P-reaction). PCR was performed on a MJResearch engine with the following cycling conditions: 95° C. for 3 min (denaturation), 94° C. for 20 s, 60° C. for 20 s and 72° C. for 70 s (36 cycles) and 72° C. for 5 min (final extension). PCR-products were analyzed using 3% agarose gel electrophoresis and the ethidium bromide stained gel was scanned using a Typhoon 9200 Imager (Amersham/Pharmacia).

6. Sodium Bisulfite Sequencing

Modification of DNA with sodium bisulfite was performed as previously described. Bisulfite-treated DNA was amplified in a nested PCR reaction using the primers icsbp-out S (5'-GGG GTA GTT AGT TTT TGG TTG-3') (SEQ ID NO: 16) and icsbp-out AS (5'-ATA MT AAT TCC ACC CCC AC-3') (SEQ ID NO: 17) for the first and icsbp-in S (5'-TTG TGG ATT TTG ATT MT GGG-3') (SEQ ID NO: 18) and icsbp-in AS (5'-CCR CCC ACT ATA CCT ACC TAC C-3') (SEQ ID NO: 19) for the second round of amplification. PCR-products were cloned using TOPO-TA Cloning Kit (Invitrogen) and several independent clones were sequenced.

7. RNA-preparation, Real-time-PCR

Total RNA was isolated from different cell lines by the guanidine thiocyanate/acid phenol method (Chomczynski, Anal. Biochem. 162 (1987), 156-159. RNA (2 µg) was reverse transcribed using Superscript II MMLV-RT (Invitrogen). Real-time PCR was performed on a Lightcycler (Roche) using the Quantitect kit (Qiagen) according to the manufacturer's instructions. Primers used were: human ICSBP: sense 5'-CGT GGT GTG CM AGG CAG-3' (SEQ ID NO: 20), antisense 5'-CTG TTA TAG AAC TGC TGC AGC TCT C-3' (SEQ ID NO: 21); human ACTB (β-Actin): sense 5'-TGA CGG GGT TCA CCC ACA CTG TGC CCA TCT A-3' (SEQ ID NO: 22), antisense 5'-CTA GM GCA TTT GTG GTG GAC GAT GGA GGG-3' (SEQ ID NO: 23). Cycling parameters were: denaturation 95° C., 15 min, amplification 95° C., 15 s, 57° C., 20 s, 72° C., 25 s, for 50 cycles. The product size was initially controlled by agarose gel electrophoresis and melting curves were analyzed to control for specificity of the PCR reactions. ICSBP data were normalized for expression of the housekeeping gene β-actin (ACTB). The relative units were calculated from a standard curve plotting 3 different concentrations of log dilutions against the PCR cycle number (CP) at which the measured fluorescence intensity reaches a fixed value. The amplification efficiency E was calculated from the slope of the standard curve by the formula: $E = 10^{-1/slope}$. $E_{ICSBP}$ was in the range of 1.87 to 1.98, $E_{ACTB}$ ranged from 1.76 to 1.84. For each sample, data of 3 independent analyzes were averaged.

Figure 2A:
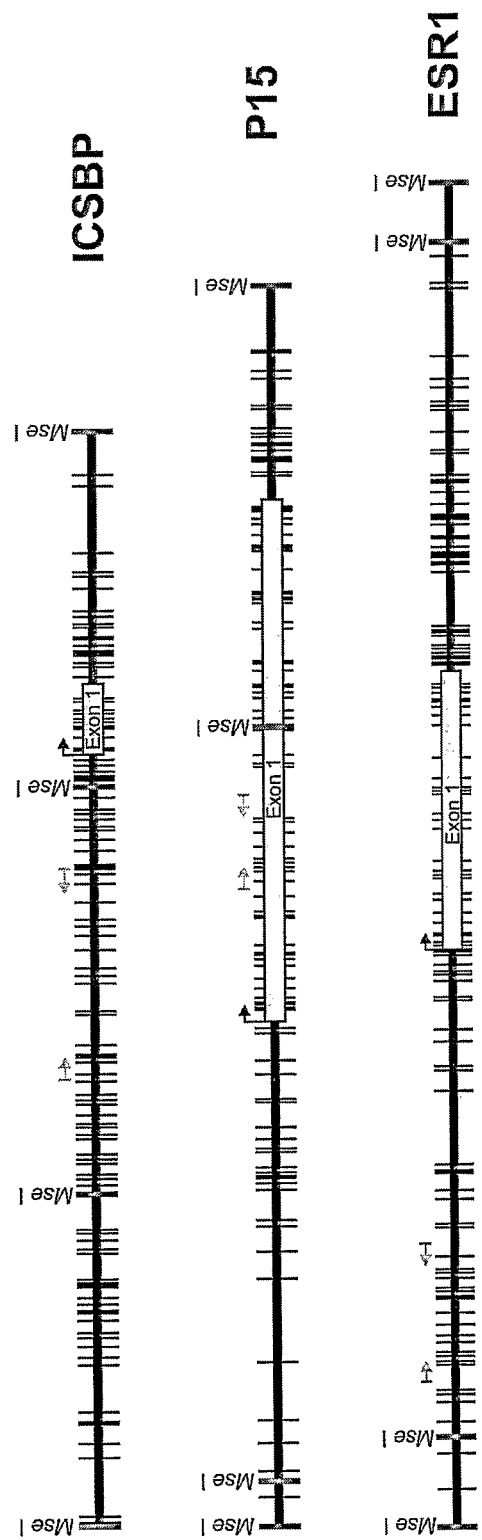
Figure 2B:
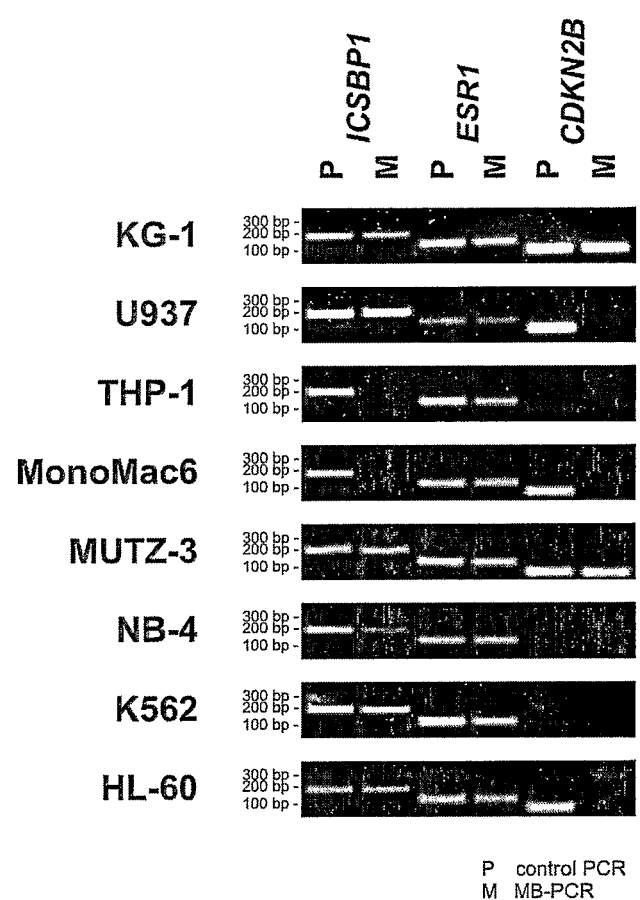

8. Analyzing the CpG Island Methylation Status of ESR1, CDKN2B (p15$^{INK4b}$), and ICSBP Promoters by MB-PCR Several leukaemia cell lines were analyzed for their CpG island methylation status of ESR1, CDKN2B (p15$^{INK4b}$), and ICSBP promoters by MB-PCR. Genomic DNA was digested with Mse I. This enzyme was chosen because it is methylation-insensitive and cuts DNA into small fragments but leaves CpG islands relatively intact. Location of the gene-specific Mse I-fragments relative to the first intron of their respective genes as well as positions of gene-specific primers used for PCR are shown in FIG. 2A. All fragments were chosen to include the putative proximal promoter regions. A total of 10 ng of restricted DNA were used for the M-reaction and 5 ng of the same digested genomic DNA were used for the P-reaction. The result of a representative MB-PCR experiment from eight different leukaemia cell lines is shown in FIG. 2B. The ESR1 promoter was amplified to varying degrees in the M-reaction of all eight samples, which is in line with previous reports demonstrating its aberrant methylation in 86% of human haematopoietic tumours. The P-reaction for the CDKN2B (p15$^{INK4b}$) promoter failed completely in three cell lines (THP-1, NB-4, K562) suggesting mutations or deletions on both alleles, which has also been demonstrated before. Two cell lines (KG-1 and MUTZ3) showed a positive M-reaction for the CDKN2B (p15$^{INK4b}$) promoter, whereas three cell lines (U937, MonoMac6, HL-60) were negative. The observed results were in good concordance with previously published methylation analyzes of ESR1 and CDKN2B (p15$^{INK4b}$) promoters in some of these cell lines. In some cases, P-reactions were weaker in comparison with other cell types, suggesting the loss or mutation of one allele (e.g. ESR1 in U937 cells). The ICSBP promoter was also amplified in M-reactions of six cell lines.

The degree and effect of ICSBP promoter methylation was analyzed to further validate the experimental potential of MB-PCR. Expression levels of ICSBP were analyzed in the eight leukaemia cell lines using LightCycler Real time PCR. As shown in FIG. 3A, mRNA expression levels inversely correlated with methylation degree as determined by MB-PCR. Treatment of U937 cells, which show a high degree of ICSBP promoter methylation with the demethylating agent Decitabine (5-Aza-2'Deoxycytidine) led to a marked, dose- and time-dependent induction of ICSBP mRNA expression (s. FIG. 3B), indicating that the methylation-induced repression of ICSBP transcription is reversible in these cells.

To test whether MB-PCR is also able to detect the methylation of CpG island promoters in primary tumour cells, DNA was prepared from blood monocytes of healthy individuals (n=4) and blast cells of patients with AML (n=11), digested with Mse I, and subjected to MB-PCR. As shown in FIG. 4, no significant level of methylation was detected in the DNA of healthy donors, whereas most patients showed significant methylation in at least one of the three promoters analyzed.

To determine how MB-PCR results correlate with the exact pattern of CpG methylation at the ICSBP promoter, ICSBP promoter methylation was analyzed by bisulfite sequencing in selected cell lines, normal and tumour cells. The results shown in FIG. 5 indicate that the degree of promoter methylation can be predicted by MB-PCR—strong amplification signals appear to indicate a high degree, whereas weaker signals indicate a lesser degree of methylation.

Figure 6A:
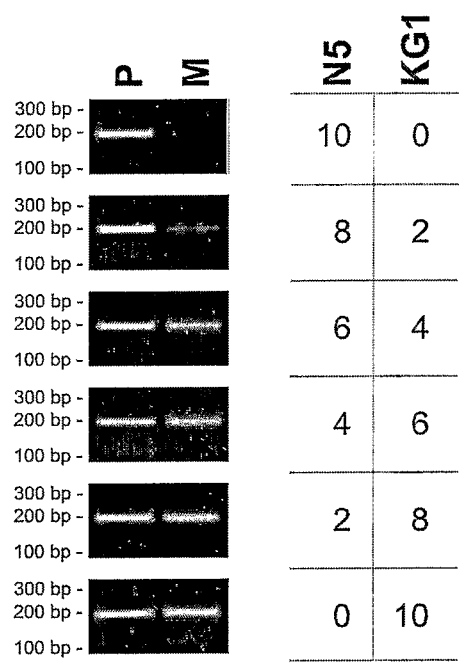
Figure 6B:
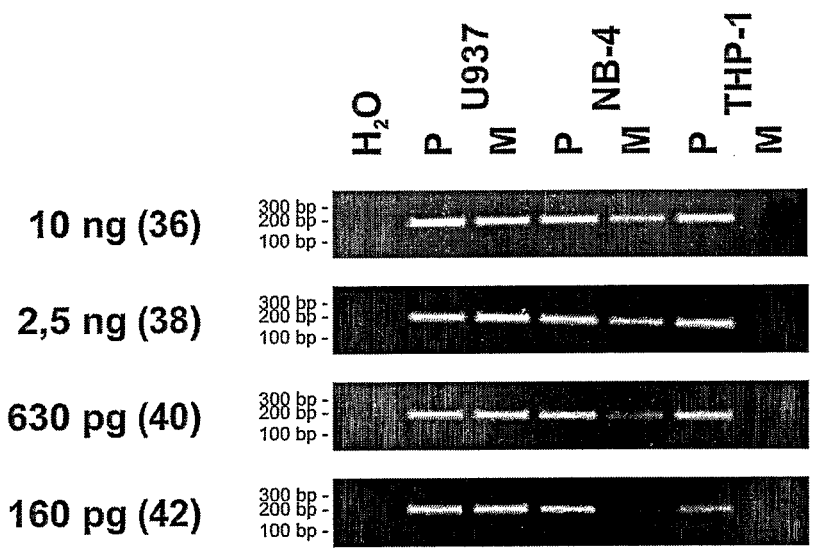

Since patient samples may be contaminated with normal, potentially unmethylated cells, the effect of increasing amounts of normal DNA in a DNA sample of a tumor cell line was determined. Restricted DNA was mixed and subjected to MB-PCR. The results are shown in FIG. 6A. The signal in the M-reaction decreased in a linear fashion with increasing amounts of normal, unmethylated DNA in the sample. To test the sensitivity of the method, MB-PCR experiments using decreasing amounts of DNA were performed. As shown in FIG. 6B, comparable results were obtained using all concentrations tested (10 ng-160 pg) when analyzing the methylation status of the ICSBP locus in three different cell lines. These results indicate, that MB-PCR can detect methylated DNA-fragments in mixtures of normal and tumour cells and works within the normal sensitivity range of standard genomic PCR (down to 160 pg of DNA).

9. Analyzing the CpG Island Methylation Status of ESR1, CDKN2B (p15$^{INK4b}$), ICSBP, ETV3 and DDX20 Promoters by MB-PCR, In another experiment, the MB-PCR method was explored by analyzing the degree of CpG methylation of single CpG island promoters that were previously shown to be frequently methylated in leukaemia cells, namely the human CDKN2B gene (also known as p15$_{INK4b}$) and the human estrogen receptor 1 (ESR1) gene. In addition to the well established tumor markers three additional genes with CpG island promoters that could potentially act as tumor suppressor genes were selected: the human interferon consensus binding protein (ICSBP) gene, the human Ets variant 3 gene (ETV3), and the human DEAD box polypeptide 20 gene (DDX20). ICSBP, a transcription factor of the interferon (IFN) regulatory factor family (IRF), is frequently down-regulated in human myeloid leukaemia (Schmidt, Blood 91 (1991), 22-29) and ICSBP-deficient mice display hematological alterations similar to chronic myelogenous leukaemia (CML) in humans (Holtschke, Cell 87 (1996), 307-317), suggesting a tumor suppressor function for ICSBP in hemopoietic cells. In mice, the Ets repressor ETV3 (also known as METS or PEI) and its co-repressor DDX20 (also known as DP103) were shown to link terminal monocytic differentiation to cell cycle arrest (Klappacher, Cell 109 (2002), 169-180), which may also indicate a possible tumor suppressor role. As a validation of our approach, genomic DNA from normal cells was either left untreated or methylated in vitro using SssI, digested with MseI and subjected to MB-PCR. Genomic DNA was digested with MseI because this enzyme is methylation-insensitive and cuts DNA into small fragments while leaving CpG islands relatively intact (Cross, Nat. Genet. 6 (1994), 236-244). Locations of the gene-specific MseI-fragments relative to the first intron of their respective genes as well as positions of gene-specific primers used for MB-PCR are shown in FIG. 8A. All fragments include the putative proximal promoter regions. As shown in FIG. 8B, the M-reactions of all five loci were negative when normal DNA was used, indicating that these genomic regions are, as expected, free of methylation in normal blood cells. However, each locus was amplified in the corresponding M-reaction when the same DNA was in vitro methylated using SssI-methylase before it was subjected to MB-PCR. Hence, MB-PCR is able to discriminate the methylated and unmethylated state at these loci.

10. Methylation Status of Specific CpG Island Promoters in Tumour Cell Lines Analyzed by MB-PCR.

In another experiment it was tested whether MB-PCR is able to detect the methylation status of the above loci in biological samples, several leukaemia cell lines were analyzed. Routinely, a total of 10 ng of restricted DNA was used for the M-reaction and 5 ng of the same digested genomic DNA was used for the P-reaction. The result of a representative MB-PCR experiment from eight different leukaemia cell lines is shown in FIG. 9A. The ESR1 promoter was amplified to varying degrees in the M-reaction of all eight samples, which is in line with previous reports demonstrating its aberrant methylation in more than 80% of human hemopoietic tumors. The P-reaction for the CDKN2B promoter failed completely in three cell lines (THP-1, NB-4, K562) suggesting mutations or deletions on both alleles, which has been demonstrated previously in the cases of NB-4 (Chim, Ann. Hematol. 82 (2003), 738-742) and K562 (Paz, Cancer Res. 63 (2003), 1114-1121). The two cell lines KG-1 and MUTZ3 showed a positive M-reaction for the CDKN2B promoter, whereas three cell lines (U937, MonoMac6, HL-60) were negative. The observed results were in good concordance with previously published methylation analyses of ESR1 (27) and CDKN2B promoters (Cameroon, Blood 94 (1999), 2445-2451; Chim (2003), loc. cit.; Paz (2003), loc. cit.). In some cases, P-reactions were weaker in comparison with other cell types, suggesting the loss or mutation of one allele (e.g. ESR1 in U937 cells). Interestingly, the ICSBP promoter was also amplified in M-reactions of six cell lines, whereas no significant methylation was detected at the promoters of ETV3 and DDX20 genes.

To determine how MB-PCR results correlate with the exact pattern of CpG methylation at the ICSBP promoter in individual cell lines, the ICSBP promoter methylation was analyzed by bisulfite sequencing. The results shown in FIG. 9B indicate that the degree of promoter methylation corresponds with results obtained by MB-PCR. Strong amplification signals (comparable to the corresponding P-reaction) as seen in KG-1, U937, MUTZ-3, HL-60, and K562 cell lines, appear to indicate a high degree, whereas weaker signals (as observed for NB-4 cells) indicate a lesser degree of methylation. In the absence of DNA methylation (THP-1 and MonoMac6 cells) the MB-PCR is negative.

11. Detecting Methylation of CpG Island Promoters in Primary Tumor Cells.

DNA was prepared from blood monocytes of several healthy persons (n=4) and leukaemic blasts of patients with previously untreated AML (n=35), digested with MseI, and subjected to MB-PCR. FIG. 11 shows representative ICSBP MB-PCR and corresponding bisulfite sequencing results for 9 AML patients and 1 normal individual. In general, the intensity of the band observed in the M-reaction (as compared to the corresponding P-reaction) showed good correlation with the mean density of methylation in the sample. Out of 35 AML-patients tested, 7 patients (20%) showed positive MB-PCR results for ICSBP, 21 patients (60%) for ESR1 and 25 patients (71%) for CDKN2B (data not shown). The frequencies for ESR1 and CDKN2B methylation observed concur with those described in previous studies. ICSBP methylation apparently only affects a subgroup of patients. Twelve patients were tested for methylation of ETV3 and DDX20 genes and, as observed for the leukaemia cell lines, no significant methylation was detected in any of the samples.

The invention claimed is:

1. An in vitro method for detecting methylated DNA comprising:
   (a) contacting a polypeptide that is capable of specifically binding methylated DNA with a sample comprising methylated and/or unmethylated DNA, wherein said polypeptide has been coated on a container; and
   b) detecting the binding of said polypeptide to methylated DNA, wherein said polypeptide has been selected from the group consisting of:
   (i) MBD2;
   (ii) a fragment of the polypeptide of (i), wherein said fragment is capable of binding methylated DNA; and
   (iii) a polypeptide that is at least 70% homologous to the polypeptide of (i) or the fragment of (i) and is capable of binding methylated DNA: and
   wherein said polypeptide is fused to an Fc-portion of an antibody through a flexible linker comprising amino acids 116 to 129 of SEQ ID NO:2.

2. The method of claim 1, wherein step (b) comprises restriction enzyme digestion, bisulfite sequencing, pyrosequencing, Southern Blot, or PCR.

3. The method of claim 1, wherein step (b) comprises PCR.

4. The method of claim 1, further comprising step (c) analyzing the methylated DNA.

5. The method of claim 4, wherein said analyzing said methylated DNA comprises sequencing.

6. The method of claim 1, wherein said container is coated directly or indirectly with said polypeptide.

7. The method of claim 1, wherein said sample is from a subject.

8. The method of claim 7, wherein said subject is suspected to have hypo-and/or hypermethylated gene loci.

9. The method of claim 8, wherein said hypo-and/or hypermethylated gene loci are indicative of a cancer, tumor or metastasis.

10. The method of claim 1, wherein the methylated DNA is less than about 10 ng.

11. The method of claim 1, wherein the polypeptide is at least 80% homologous to a polypeptide of (i) or a fragment of (ii) and is capable of binding methylated DNA.

12. The method of claim 1, wherein the polypeptide is at least 85% homologous to a polypeptide of (i) or a fragment of (ii) and is capable of binding methylated DNA.

13. The method of claim 1, wherein the polypeptide is at least 90% homologous to a polypeptide of (i) or a fragment of (ii) and is capable of binding methylated DNA.

14. The method of claim 1, wherein the polypeptide is at least 95% homologous to a polypeptide of (i) or a fragment of (ii) and is capable of binding methylated DNA.

15. The method of claim 1, wherein MBD2 is human MBD2.

16. The method of claim 1, wherein MBD2 comprises amino acids 29 to 115 of SEQ ID NO:2.

* * * * *

SEQUENCE LISTING

<160> NUMBER OF SEQ ID NOS: 23

<210> SEQ ID NO 1
<211> LENGTH: 4598
<212> TYPE: DNA
<213> ORGANISM: Homo sapiens
<220> FEATURE:
<221> NAME/KEY: CDS
<222> LOCATION: (851)..(1933)

<400> SEQUENCE: 1

```
tcgcgcgttt  cggtgatgac  ggtgaaaacc  tctgacacat  gcagctcccg  gagacggtca      60
cagcttgtct  gtaagcggat  gccgggagca  gacaagcccg  tcagggcgcg  tcagcgggtg     120
ttggcgggtg  tcggggctgg  cttaactatg  cggcatcaga  gcagattgta  ctgagagtgc     180
accatatgcg  gtgtgaaata  ccgcacagat  gcgtaaggag  aaaataccgc  atcaggcgcc     240
attcgccatt  caggctgcgc  aactgttggg  aagggcgatc  ggtgcgggcc  tcttcgctat     300
tacgccagct  ggcgaaaggg  ggatgtgctg  caaggcgatt  aagttgggta  acgccagggt     360
tttcccagtc  acgacgttgt  aaaacgacgg  ccagtgccag  tgaattttaa  cgttgcagga     420
caggatgtgg  tgcccgatgt  gactagctct  ttgctgcagg  ccgtcctatc  ctctggttcc     480
gataagagac  ccagaactcc  ggccccccac  cgcccaccgc  caccccata   catatgtggt     540 acgcaagtaa  gagtgcctgc  gcatgcccca  tgtgcccac   caagagtttt  gcatcccata    600
caagtcccca  aagtggagaa  ccgaaccaat  tcttcgcggg  cagaacaaaa  gcttctgcac    660
acgtctccac  tcgaatttgg  agccgccgg   cgtgtgcaaa  agaggtgaat  cgaacgaaag    720
acccgtgtgt  aaagccgcgt  ttccaaaatg  tataaaaccg  agagcatctg  gccaatgtgc    780
atcagttgtg  gtcagcagca  aaatcaagtg  aatcatctca  gtgcaactaa  aggggggatc    840
cgatctcaat atg aag tta tgc ata tta ctg gcc gtc gtg gcc ttt gtt              889
           Met Lys Leu Cys Ile Leu Leu Ala Val Val Ala Phe Val
           1               5                   10 ggc ctc tcg ctc ggg aga tct cca tgg ccc ggg gta cct act agc acg              937
Gly Leu Ser Leu Gly Arg Ser Pro Trp Pro Gly Val Pro Thr Ser Thr
```

```
              15                  20                  25
gag agc ggg aag agg atg gat tgc ccg gcc ctc ccc ccc gga tgg aag      985
Glu Ser Gly Lys Arg Met Asp Cys Pro Ala Leu Pro Pro Gly Trp Lys
30                  35                  40                  45 aag gag gaa gtg atc cga aaa tct ggg cta agt gct ggc aag agc gat     1033
Lys Glu Glu Val Ile Arg Lys Ser Gly Leu Ser Ala Gly Lys Ser Asp
                50                  55                  60 gtc tac tac ttc agt cca agt ggt aag aag ttc aga agc aag cct cag     1081
Val Tyr Tyr Phe Ser Pro Ser Gly Lys Lys Phe Arg Ser Lys Pro Gln
                65                  70                  75 ttg gca agg tac ctg gga aat act gtt gat ctc agc agt ttt gac ttc     1129
Leu Ala Arg Tyr Leu Gly Asn Thr Val Asp Leu Ser Ser Phe Asp Phe
            80                  85                  90 aga act gga aag atg atg cct agt aaa tta cag aag aac aaa cag aga     1177
Arg Thr Gly Lys Met Met Pro Ser Lys Leu Gln Lys Asn Lys Gln Arg
        95                  100                 105 ctg cga aac gat cct ctg gcg gcc gcg gat ccc atc gaa ggt cgt ggt     1225
Leu Arg Asn Asp Pro Leu Ala Ala Ala Asp Pro Ile Glu Gly Arg Gly
110                 115                 120                 125 ggt ggt ggt ggt gat ccc aaa tct tgt gac aaa cct cac aca tgc cca     1273
Gly Gly Gly Gly Asp Pro Lys Ser Cys Asp Lys Pro His Thr Cys Pro
                130                 135                 140 ctg tgc cca gca cct gaa ctc ctg ggg gga ccg tca gtc ttc ctc ttc     1321
Leu Cys Pro Ala Pro Glu Leu Leu Gly Gly Pro Ser Val Phe Leu Phe
                145                 150                 155 ccc cca aaa ccc aag gac acc ctc atg atc tcc cgg acc cct gag gtc     1369
Pro Pro Lys Pro Lys Asp Thr Leu Met Ile Ser Arg Thr Pro Glu Val
                160                 165                 170 aca tgc gtg gtg gtg gac gtg agc cac gaa gac cct gag gtc aag ttc     1417
Thr Cys Val Val Val Asp Val Ser His Glu Asp Pro Glu Val Lys Phe
    175                 180                 185 aac tgg tac gtg gac ggc gtg gag gtg cat aat gcc aag aca aag ccg     1465
Asn Trp Tyr Val Asp Gly Val Glu Val His Asn Ala Lys Thr Lys Pro
190                 195                 200                 205 cgg gag gag cag tac aac agc acg tac cgt gtg gtc agc gtc ctc acc     1513
Arg Glu Glu Gln Tyr Asn Ser Thr Tyr Arg Val Val Ser Val Leu Thr
                210                 215                 220 gtc ctg cac cag gac tgg ctg aat ggc aag gag tac aag tgc aag gtc     1561
Val Leu His Gln Asp Trp Leu Asn Gly Lys Glu Tyr Lys Cys Lys Val
                225                 230                 235 tcc aac aaa gcc ctc cca gcc ccc atc gag aaa acc atc tcc aaa gcc     1609
Ser Asn Lys Ala Leu Pro Ala Pro Ile Glu Lys Thr Ile Ser Lys Ala
            240                 245                 250 aaa ggg cag ccc cga gaa cca cag gtg tac acc ctg ccc cca tcc cgg     1657
Lys Gly Gln Pro Arg Glu Pro Gln Val Tyr Thr Leu Pro Pro Ser Arg
        255                 260                 265 gat gag ctg acc aag aac cag gtc agc ctg acc tgc cta gtc aaa ggc     1705
Asp Glu Leu Thr Lys Asn Gln Val Ser Leu Thr Cys Leu Val Lys Gly
270                 275                 280                 285 ttc tat ccc agc gac atc gcc gtg gag tgg gag agc aat ggg cag ccg     1753
Phe Tyr Pro Ser Asp Ile Ala Val Glu Trp Glu Ser Asn Gly Gln Pro
                290                 295                 300 gag aac aac tac aag gcc acg cct ccc gtg ctg gac tcc gac ggc tcc     1801
Glu Asn Asn Tyr Lys Ala Thr Pro Pro Val Leu Asp Ser Asp Gly Ser
                305                 310                 315 ttc ttc ctc tac agc aag ctc acc gtg gac aag agc agg tgg cag cag     1849
Phe Phe Leu Tyr Ser Lys Leu Thr Val Asp Lys Ser Arg Trp Gln Gln
                320                 325                 330 ggg aac gtc ttc tca tgc tcc gtg atg cat gag gct ctg cac aac cac     1897
```

```
Gly Asn Val Phe Ser Cys Ser Val Met His Glu Ala Leu His Asn His
335                 340                 345 tac acg cag aag agc ctc tcc ctg tct ccg ggt aaa tgagctagag         1943
Tyr Thr Gln Lys Ser Leu Ser Leu Ser Pro Gly Lys
350                 355                 360 ggcccgcggt tcgaaggtaa gcctatccct aaccctctcc tcggtctcga ttctacgcgt    2003
accggtcatc atcaccatca ccattgagtt taaacccgct gatcagcctc gactgtgcct    2063
tctaaggcct gagctcgctg atcagcctcg atcgaggatc cagacatgat aagatacatt    2123
gatgagtttg gacaaaccac aactagaatg cagtgaaaaa aatgctttat ttgtgaaatt    2183
tgtgatgcta ttgctttatt tgtaaccatt ataagctgca ataaacaagt taacaacaac    2243
aattgcattc attttatgtt tcaggttcag ggggaggtgt gggaggtttt ttaaagcaag    2303
taaaacctct acaaatgtgg tatggctgat tatgatcagt cgacctgcag gcatgcaagc    2363
ttggcgtaat catggtcata gctgtttcct gtgtgaaatt gttatccgct cacaattcca    2423
cacaacatac gagccggaag cataaagtgt aaagcctggg gtgcctaatg agtgagctaa    2483
ctcacattaa ttgcgttgcg ctcactgccc gctttccagt cgggaaacct gtcgtgccag    2543
ctgcattaat gaatcggcca acgcgcgggg agaggcggtt tgcgtattgg gcgctcttcc    2603
gcttcctcgc tcactgactc gctgcgctcg tcgttcggc tgcggcgagc ggtatcagct     2663
cactcaaagg cggtaatacg gttatccaca gaatcagggg ataacgcagg aagaacatg     2723
tgagcaaaag gccagcaaaa ggccaggaac cgtaaaaagg ccgcgttgct ggcgtttttc    2783
cataggctcc gccccctga cgagcatcac aaaaatcgac gctcaagtca gaggtggcga     2843
aacccgacag gactataaag ataccaggcg tttccccctg gaagctccct cgtgcgctct    2903
cctgttccga ccctgccgct taccggatac ctgtccgcct ttctcccttc gggaagcgtg    2963
gcgctttctc atagctcacg ctgtaggtat ctcagttcgg tgtaggtcgt tcgctccaag    3023
ctgggctgtg tgcacgaacc ccccgttcag cccgaccgct gcgccttatc cggtaactat    3083
cgtcttgagt ccaacccggt aagacacgac ttatcgccac tggcagcagc cactggtaac    3143
aggattagca gagcgaggta tgtaggcggt gctacagagt tcttgaagtg gtggcctaac    3203
tacggctaca ctagaaggac agtatttggt atctgcgctc tgctgaagcc agttaccttc    3263
ggaaaaagag ttggtagctc ttgatccggc aaacaaacca ccgctggtag cggtggtttt    3323
tttgtttgca agcagcagat tacgcgcaga aaaaaaggat ctcaagaaga tcctttgatc    3383
ttttctacgg ggtctgacgc tcagtggaac gaaaactcac gttaagggat tttggtcatg    3443
agattatcaa aaaggatctt cacctagatc cttttaaatt aaaaatgaag ttttaaatca    3503
atctaaagta tatatgagta aacttggtct gacagttacc aatgcttaat cagtgaggca    3563
cctatctcag cgatctgtct atttcgttca tccatagttg cctgactccc cgtcgtgtag    3623
ataactacga tacgggaggg cttaccatct ggccccagtg ctgcaatgat accgcgagac    3683
ccacgctcac cggctccaga tttatcagca ataaaccagc cagccggaag ggccgagcgc    3743
agaagtggtc ctgcaacttt atccgcctcc atccagtcta ttaattgttg ccgggaagct    3803
agagtaagta gttcgccagt taatagtttg cgcaacgttg ttgccattgc tacaggcatc    3863
gtggtgtcac gctcgtcgtt tggtatggct tcattcagct ccggttccca acgatcaagg    3923
cgagttacat gatcccccat gttgtgcaaa aaagcggtta gctccttcgg tcctccgatc    3983
gttgtcagaa gtaagttggc cgcagtgtta tcactcatgg ttatggcagc actgcataat    4043
tctcttactg tcatgccatc cgtaagatgc ttttctgtga ctggtgagta ctcaaccaag    4103
```

-continued

```
tcattctgag aatagtgtat gcggcgaccg agttgctctt gcccggcgtc aatacgggat   4163
aataccgcgc cacatagcag aactttaaaa gtgctcatca ttggaaaacg ttcttcgggg   4223
cgaaaactct caaggatctt accgctgttg agatccagtt cgatgtaacc cactcgtgca   4283
cccaactgat cttcagcatc ttttactttc accagcgttt ctgggtgagc aaaaacagga   4343
aggcaaaatg ccgcaaaaaa gggaataagg gcgacacgga aatgttgaat actcatactc   4403 ttccttttc aatattattg aagcatttat cagggttatt gtctcatgag cggatacata    4463
tttgaatgta tttagaaaaa taaacaaata ggggttccgc gcacatttcc ccgaaaagtg   4523
ccacctgacg tctaagaaac cattattatc atgacattaa cctataaaaa taggcgtatc   4583
acgaggccct ttcgt                                                    4598
```

<210> SEQ ID NO 2
<211> LENGTH: 361
<212> TYPE: PRT
<213> ORGANISM: Homo sapiens

<400> SEQUENCE: 2

```
Met Lys Leu Cys Ile Leu Leu Ala Val Val Ala Phe Val Gly Leu Ser
1               5                   10                  15

Leu Gly Arg Ser Pro Trp Pro Gly Val Pro Thr Ser Thr Glu Ser Gly
            20                  25                  30

Lys Arg Met Asp Cys Pro Ala Leu Pro Pro Gly Trp Lys Lys Glu Glu
        35                  40                  45

Val Ile Arg Lys Ser Gly Leu Ser Ala Gly Lys Ser Asp Val Tyr Tyr
    50                  55                  60

Phe Ser Pro Ser Gly Lys Lys Phe Arg Ser Lys Pro Gln Leu Ala Arg
65                  70                  75                  80

Tyr Leu Gly Asn Thr Val Asp Leu Ser Ser Phe Asp Phe Arg Thr Gly
                85                  90                  95

Lys Met Met Pro Ser Lys Leu Gln Lys Asn Lys Gln Arg Leu Arg Asn
            100                 105                 110

Asp Pro Leu Ala Ala Ala Asp Pro Ile Glu Gly Arg Gly Gly Gly Gly
        115                 120                 125

Gly Asp Pro Lys Ser Cys Asp Lys Pro His Thr Cys Pro Leu Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285
```

Ser Asp Ile Ala Val Glu Trp Glu Ser Asn Gly Gln Pro Glu Asn Asn
    290                 295                 300

Tyr Lys Ala Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
            355                 360

<210> SEQ ID NO 3
<211> LENGTH: 361
<212> TYPE: PRT
<213> ORGANISM: Homo sapiens

<400> SEQUENCE: 3

Met Lys Leu Cys Ile Leu Leu Ala Val Val Ala Phe Val Gly Leu Ser
1               5                   10                  15

Leu Gly Arg Ser Pro Trp Pro Gly Val Pro Thr Ser Thr Glu Ser Gly
            20                  25                  30

Lys Arg Met Asp Cys Pro Ala Leu Pro Pro Gly Trp Lys Lys Glu Glu
        35                  40                  45

Val Ile Arg Lys Ser Gly Leu Ser Ala Gly Lys Ser Asp Val Tyr Tyr
    50                  55                  60

Phe Ser Pro Ser Gly Lys Lys Phe Arg Ser Lys Pro Gln Leu Ala Arg
65                  70                  75                  80

Tyr Leu Gly Asn Thr Val Asp Leu Ser Ser Phe Asp Phe Arg Thr Gly
                85                  90                  95

Lys Met Met Pro Ser Lys Leu Gln Lys Asn Lys Gln Arg Leu Arg Asn
            100                 105                 110

Asp Pro Leu Ala Ala Asp Pro Ile Glu Gly Arg Gly Gly Gly Gly
            115                 120                 125

Gly Asp Pro Lys Ser Cys Asp Lys Pro His Thr Cys Pro Leu Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn

```
            290                 295                 300
Tyr Lys Ala Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
            325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360
```

```
<210> SEQ ID NO 4
<211> LENGTH: 28
<212> TYPE: DNA
<213> ORGANISM: artificial sequence
<220> FEATURE:
<223> OTHER INFORMATION: Primer, human MDB2 gene

<400> SEQUENCE: 4
agatgctagc acggagagcg ggaagagg                                    28

<210> SEQ ID NO 5
<211> LENGTH: 35
<212> TYPE: DNA
<213> ORGANISM: artificial sequence
<220> FEATURE:
<223> OTHER INFORMATION: Primer, human MDB2 gene

<400> SEQUENCE: 5
atcacgcggc cgccagagga tcgtttcgca gtctc                            35

<210> SEQ ID NO 6
<211> LENGTH: 21
<212> TYPE: DNA
<213> ORGANISM: artificial sequence
<220> FEATURE:
<223> OTHER INFORMATION: Primer, human p15 gene

<400> SEQUENCE: 6
ggctcagctt cattaccctc c                                           21

<210> SEQ ID NO 7
<211> LENGTH: 19
<212> TYPE: DNA
<213> ORGANISM: artificial sequence
<220> FEATURE:
<223> OTHER INFORMATION: Primer, human p15 gene

<400> SEQUENCE: 7
aaagcccgga gctaacgac                                              19

<210> SEQ ID NO 8
<211> LENGTH: 19
<212> TYPE: DNA
<213> ORGANISM: artificial sequence
<220> FEATURE:
<223> OTHER INFORMATION: Primer, human ESR1 gene

<400> SEQUENCE: 8
gactgcactt gctcccgtc                                              19

<210> SEQ ID NO 9
<211> LENGTH: 21
<212> TYPE: DNA
<213> ORGANISM: artificial sequence
```

```
<220> FEATURE:
<223> OTHER INFORMATION: Primer, human ESR1 gene

<400> SEQUENCE: 9
aagagcacag cccgaggtta g                                          21

<210> SEQ ID NO 10
<211> LENGTH: 19
<212> TYPE: DNA
<213> ORGANISM: artificial sequence
<220> FEATURE:
<223> OTHER INFORMATION: Primer, human ICSBP gene

<400> SEQUENCE: 10
cggaattcct gggaaagcc                                             19

<210> SEQ ID NO 11
<211> LENGTH: 21
<212> TYPE: DNA
<213> ORGANISM: artificial sequence
<220> FEATURE:
<223> OTHER INFORMATION: Primer, human ICSBP gene

<400> SEQUENCE: 11
ttccgagaaa tcactttccc g                                          21

<210> SEQ ID NO 12
<211> LENGTH: 21
<212> TYPE: DNA
<213> ORGANISM: artificial sequence
<220> FEATURE:
<223> OTHER INFORMATION: Primer, human METS gene

<400> SEQUENCE: 12
aattgcgtct gaagtctgcg g                                          21

<210> SEQ ID NO 13
<211> LENGTH: 20
<212> TYPE: DNA
<213> ORGANISM: artificial sequence
<220> FEATURE:
<223> OTHER INFORMATION: Primer, human METS gene

<400> SEQUENCE: 13
tcccacacaa cagagaggcg                                            20

<210> SEQ ID NO 14
<211> LENGTH: 24
<212> TYPE: DNA
<213> ORGANISM: artificial sequence
<220> FEATURE:
<223> OTHER INFORMATION: Primer, human DP103 gene

<400> SEQUENCE: 14
gctgttagtc cagttccagg ttcc                                       24

<210> SEQ ID NO 15
<211> LENGTH: 22
<212> TYPE: DNA
<213> ORGANISM: artificial sequence
<220> FEATURE:
<223> OTHER INFORMATION: Primer, human DP103 gene

<400> SEQUENCE: 15
gtgcaaccac atttatctcc gg                                         22
```

<210> SEQ ID NO 16
<211> LENGTH: 21
<212> TYPE: DNA
<213> ORGANISM: artificial sequence
<220> FEATURE:
<223> OTHER INFORMATION: Primer, human ICSBP gene

<400> SEQUENCE: 16
ggggtagtta gttttggtt g                                       21

<210> SEQ ID NO 17
<211> LENGTH: 20
<212> TYPE: DNA
<213> ORGANISM: artificial sequence
<220> FEATURE:
<223> OTHER INFORMATION: Primer, human ICSBP gene

<400> SEQUENCE: 17
ataaataatt ccacccccac                                        20

<210> SEQ ID NO 18
<211> LENGTH: 21
<212> TYPE: DNA
<213> ORGANISM: artificial sequence
<220> FEATURE:
<223> OTHER INFORMATION: Primer, human ICSBP gene

<400> SEQUENCE: 18
ttgtggattt tgattaatgg g                                      21

<210> SEQ ID NO 19
<211> LENGTH: 22
<212> TYPE: DNA
<213> ORGANISM: artificial sequence
<220> FEATURE:
<223> OTHER INFORMATION: Primer, human ICSBP gene

<400> SEQUENCE: 19
ccrcccacta tacctaccta cc                                     22

<210> SEQ ID NO 20
<211> LENGTH: 18
<212> TYPE: DNA
<213> ORGANISM: artificial sequence
<220> FEATURE:
<223> OTHER INFORMATION: Primer, human ICSBP gene

<400> SEQUENCE: 20
cgtggtgtgc aaaggcag                                          18

<210> SEQ ID NO 21
<211> LENGTH: 25
<212> TYPE: DNA
<213> ORGANISM: artificial sequence
<220> FEATURE:
<223> OTHER INFORMATION: Primer, human ICSBP gene

<400> SEQUENCE: 21
ctgttataga actgctgcag ctctc                                  25

<210> SEQ ID NO 22
<211> LENGTH: 31
<212> TYPE: DNA
<213> ORGANISM: artificial sequence
<220> FEATURE:
<223> OTHER INFORMATION: Primer, human ACTB -continued

```
<400> SEQUENCE: 22
tgacggggtt cacccacact gtgcccatct a                                  31

<210> SEQ ID NO 23
<211> LENGTH: 30
<212> TYPE: DNA
<213> ORGANISM: artificial sequence
<220> FEATURE:
<223> OTHER INFORMATION: Primer, human ACTB

<400> SEQUENCE: 23
ctagaagcat ttgtggtgga cgatggaggg                                    30
```